(12) United States Patent
Robinson et al.

(10) Patent No.: US 11,865,036 B2
(45) Date of Patent: Jan. 9, 2024

(54) INTEGRATED HEATER ON FACIAL SKINCARE MASK

(71) Applicant: L'Oreal, Paris (FR)

(72) Inventors: Michael Robinson, Brooklyn, NY (US); William Bickford, Scotch Plains, NJ (US)

(73) Assignee: L'Oreal, Paris (FR)

( * ) Notice: Subject to any disclaimer, the term of this patent is extended or adjusted under 35 U.S.C. 154(b) by 1118 days.

(21) Appl. No.: 16/586,608

(22) Filed: Sep. 27, 2019

(65) Prior Publication Data

US 2021/0093479 A1    Apr. 1, 2021

(51) Int. Cl.
*A61F 7/03* (2006.01)
*A61K 8/02* (2006.01)
*A61F 7/00* (2006.01)
*A61F 7/02* (2006.01)

(52) U.S. Cl.
CPC ............ *A61F 7/034* (2013.01); *A61K 8/0212* (2013.01); *A61F 2007/0003* (2013.01); *A61F 2007/0219* (2013.01); *A61F 2007/0226* (2013.01); *A61F 2007/0244* (2013.01); *A61K 2800/242* (2013.01)

(58) Field of Classification Search
CPC ............ A61K 2800/242; A61K 8/0212; A61Q 19/00; B32B 2255/10; B32B 2255/205; B32B 2262/062; B32B 2266/122; B32B 2307/724; B32B 2307/7244; B32B 2307/732; B32B 2307/748; B32B 2553/00; B32B 27/065; B32B 27/08; B32B 27/12; B32B 27/308; B32B 27/32; B32B 27/36; B32B 3/266; B32B 5/022; B32B 5/18; B32B 5/26; B32B 7/09; B32B 7/12

See application file for complete search history.

(56) References Cited

U.S. PATENT DOCUMENTS

| | | | |
|---|---|---|---|
| 6,261,595 B1 | 7/2001 | Stanley et al. | |
| 6,756,053 B2 | 6/2004 | Zhang et al. | |
| 6,893,453 B2 * | 5/2005 | Agarwal | A61F 7/034 |
| | | | 607/108 |
| 7,722,782 B2 | 5/2010 | Coffey et al. | |
| 8,133,606 B2 | 3/2012 | Coffey et al. | |
| 9,004,059 B2 | 4/2015 | Sesock et al. | |
| 9,024,360 B1 | 5/2015 | Huffer et al. | |
| 9,278,796 B2 | 3/2016 | Huffer et al. | |
| 9,642,736 B2 | 5/2017 | Laubach et al. | |
| 9,872,795 B2 | 1/2018 | Laubach et al. | |
| 10,046,325 B2 | 8/2018 | Beckerdite et al. | |
| 2010/0146849 A1 | 6/2010 | Coffey et al. | |
| 2010/0161014 A1 * | 6/2010 | Lynch | A61F 7/02 |
| | | | 607/108 |
| 2010/0163011 A1 | 7/2010 | Tinker et al. | |
| 2010/0326418 A1 | 12/2010 | Sesock et al. | |
| 2011/0218601 A1 * | 9/2011 | Uchiyama | A61F 13/0259 |
| | | | 607/112 |
| 2013/0174835 A1 | 7/2013 | Tinker et al. | |

(Continued)

*Primary Examiner* — Tigist S Demie

(74) *Attorney, Agent, or Firm* — Christensen O'Connor Johnson Kindness PLLC

(57) ABSTRACT

A package comprises a mask; and an inactive heater, wherein the mask includes at least one product layer having infused thereon at least one active, and wherein the inactive heater is located in or in proximity to the mask to transfer heat to the mask upon activation of the heater.

5 Claims, 24 Drawing Sheets

(56) References Cited

U.S. PATENT DOCUMENTS

| | | |
|---|---|---|
| 2013/0345649 A1* | 12/2013 | Stockley, III .......... A61F 7/034 |
| | | 156/196 |
| 2014/0102435 A1 | 4/2014 | Sesock et al. |
| 2014/0109889 A1 | 4/2014 | Pedicini et al. |
| 2014/0109890 A1 | 4/2014 | Pedicini et al. |
| 2015/0059729 A1 | 3/2015 | Tinker et al. |
| 2015/0232254 A1* | 8/2015 | Huffer .................... B65D 65/40 |
| | | 206/484.2 |
| 2015/0257917 A1 | 9/2015 | Laubach et al. |
| 2015/0257918 A1 | 9/2015 | Laubach et al. |
| 2016/0161149 A1 | 6/2016 | Laubach et al. |
| 2016/0279638 A1 | 9/2016 | Beckerdite et al. |
| 2017/0110765 A1 | 4/2017 | Yadav et al. |
| 2017/0207447 A1 | 7/2017 | Yadav et al. |
| 2018/0055677 A1 | 3/2018 | Laubach et al. |
| 2018/0071971 A1 | 3/2018 | Beckerdite et al. |
| 2018/0140456 A1 | 5/2018 | Laubach et al. |
| 2018/0206616 A1* | 7/2018 | Alary ...................... A61P 17/10 |
| 2018/0252438 A9 | 9/2018 | Laubach et al. |

* cited by examiner

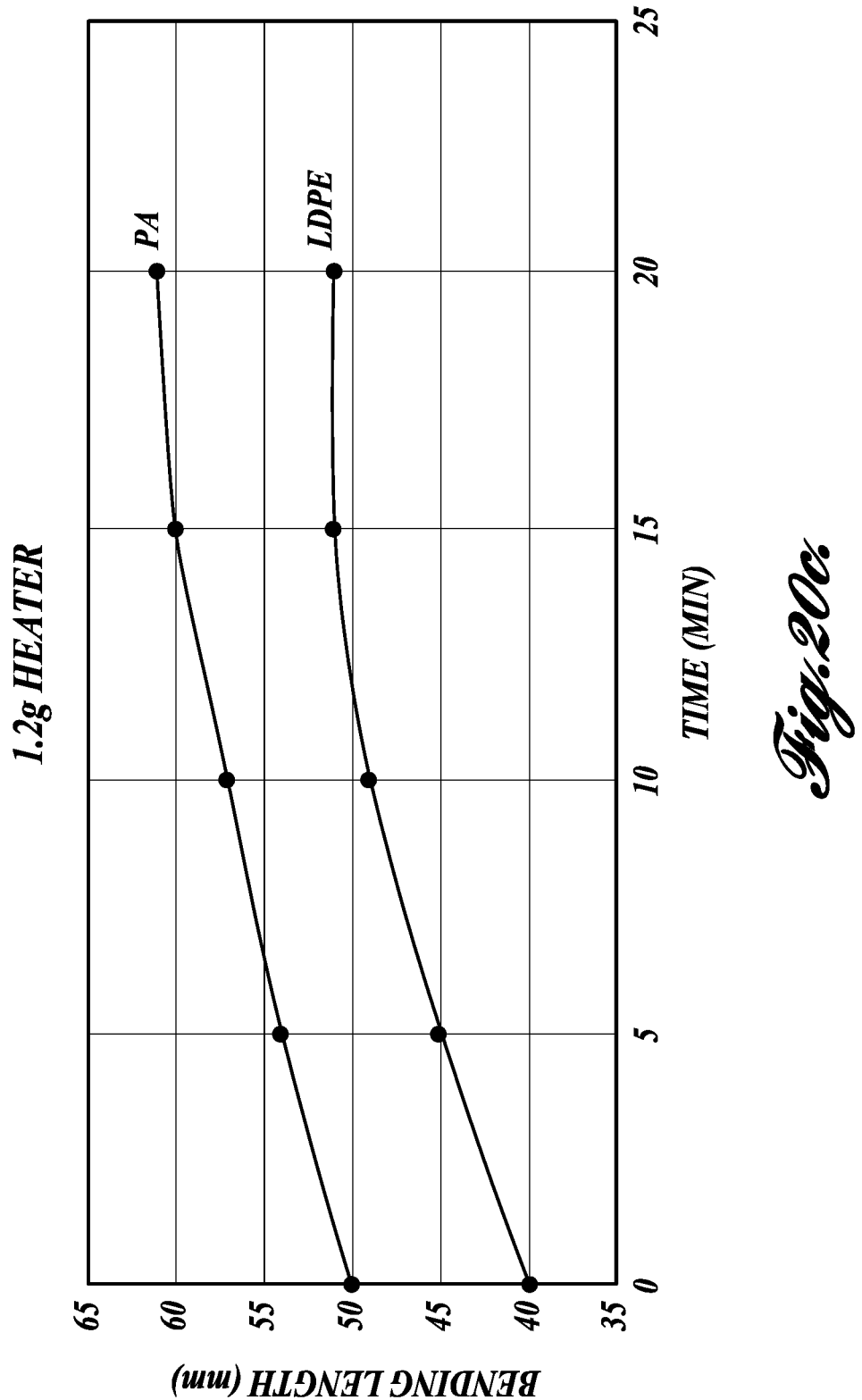

INTEGRATED HEATER ON FACIAL SKINCARE MASK

SUMMARY

In one embodiment, a package comprises a mask; and an inactive heater, wherein the mask includes at least one product layer having infused thereon at least one active, and wherein the inactive heater is located in or in proximity to the mask to transfer heat to the mask upon activation of the heater.

In one embodiment, a package comprises a film enclosing the inactive heater, wherein the film has a conformability measured by an extensibility of 20% at a force of less than 70,000 lbs or less than 10,000 lbs or less than 25,000 lbs, or a bending length over time value of 3 mm to 65 mm at 10 mins.

In one embodiment, a package comprises an adhesive layer on or the same as the product layer, wherein adhesive layer has a peel strength from 0.4 to 25 N/inch.

In one embodiment, the product layer comprises a hydrogel or silicone film for adhering to the skin.

In one embodiment, a package comprises a plurality of masks each including an inactive heater, wherein the inactive heaters include a zinc air battery that is enclosed within a barrier film with holes, each of the barrier films with holes is prescored and adhered releaseably to a common cover film.

In one embodiment, a package comprises a substrate juxtaposed next to the film with holes, the heater juxtaposed next to the substrate, a barrier film juxtaposed next to the heater, and the product layer juxtaposed next to the barrier film, wherein the product layer and cover film are exterior layers.

In one embodiment, the mask includes the inactive heater which includes a zinc air battery that is enclosed within a barrier film with holes, and a second barrier peel off film is adhered over the holes preventing air to reach the battery.

In one embodiment, a package, comprises a substrate juxtaposed next to the film with holes, the heater juxtaposed next to the substrate, a barrier film juxtaposed next to the heater, and the product layer juxtaposed next to the barrier film, wherein the product layer and peel off film are exterior layers.

In one embodiment, the mask includes the inactive heater which includes a zinc air battery that is enclosed within a barrier film with holes, and the barrier films with holes is prescored and adhered releaseably to a cover film preventing air to reach the battery.

In one embodiment, a package comprises a substrate juxtaposed next to the film with holes, the heater juxtaposed next to the substrate, a barrier film juxtaposed next to the heater, and the product layer juxtaposed next to the barrier film, wherein the product layer and cover film are exterior layers.

In one embodiment, the mask includes the inactive heater which includes a zinc air battery that is enclosed within a barrier film with holes, wherein the mask with inactive heater are enclosed in cover film envelope, wherein the barrier film with holes is juxtaposed to the cover film envelope preventing air to reach the battery.

In one embodiment, a package comprises a substrate juxtaposed next to the film with holes, the heater juxtaposed next to the substrate, and the product layer juxtaposed next to the substrate, wherein the product layer and film with holes are juxtaposed next to the opposite insides of the envelope.

In one embodiment, the mask and the inactive heater which includes a zinc air battery that is enclosed within a barrier film with holes are provided in a pouch preventing air to reach the battery, wherein the mask is juxtaposed between the barrier film with holes and the pouch.

In one embodiment, a package comprises a substrate juxtaposed next to the heater, and the film with holes is juxtaposed to the substrate, and the product layer and heater are juxtaposed next to opposite insides of the pouch.

In one embodiment, the mask and the inactive heater which includes a zinc air battery are provided in a pouch having barrier film without holes on one side and a barrier film with holes on a second side, wherein a peel off film is adhered releaseably over the holes preventing air to reach the battery, wherein the mask is juxtaposed next to the barrier film without holes.

In one embodiment, a package comprises the heater juxtaposed next to the film with holes, a substrate juxtaposed next to the heater, and the product layer juxtaposed next to the substrate, wherein the product layer and heater are juxtaposed next to opposite insides of the pouch.

In one embodiment, the mask and the inactive heater which includes a zinc air battery that is enclosed within a barrier film with holes are provided in a tray preventing air to reach the battery, wherein the mask is juxtaposed between the barrier film with holes and the pouch.

In one embodiment, a package comprises a substrate juxtaposed next to the heater, and the film with holes juxtaposed next to the substrate, and the product layer juxtaposed next to the substrate, wherein the product layer and the heater are juxtaposed next to opposite insides of the tray.

In one embodiment, a package comprises a stack of masks in a tray and a heater assembly covering the stack of masks, wherein the heater assembly includes at least one inactive heater which includes a zinc air battery enclosed in a barrier film with holes and a peel off film is adhered over the holes preventing air to reach the battery.

In one embodiment, the heater assembly further comprises a substrate juxtaposed next to the film with holes, the heater is juxtaposed next to the substrate, and a cardstock is juxtaposed next to the heater, wherein the cardstock and peel off film are exterior layers of the heater assembly.

In one embodiment, a package comprises a card capable of being folded to juxtapose a first side on a second opposite side, wherein the first side includes a mask and the inactive heater on the exterior, and the second side includes a hydrogel heat activator.

In one embodiment, a package comprises a barrier film juxtaposed next to the heater, the product layer juxtaposed next to the barrier film, and the barrier film juxtaposed next to the cardstock on the first side.

In one embodiment, a package comprises a micro-cavitated film juxtaposed next to the inactive heater, a first metallized film juxtaposed next to the micro-cavitated film, and a second metallized film juxtaposed next to a side of inactive heater without the micro-cavitated film, wherein the first metallized film is on the exterior, and the product layer comprises a hydrogel layer juxtaposed next to the second metallized film.

In one embodiment, a package comprises a release layer juxtaposed next to the hydrogel layer, wherein the release layer is on the exterior.

In one embodiment, a package comprises a micro-cavitated film juxtaposed next to the inactive heater, a first metallized film juxtaposed next to the micro-cavitated film, and a second metallized film juxtaposed next to a side of inactive heater without the micro-cavitated film, wherein the first metallized film is on the exterior, and the product layer comprises a silicone layer juxtaposed next to carrier film, wherein an acrylic adhesive layer is juxtaposed between the carrier film and the second metallized film.

In one embodiment, a package comprises a release layer juxtaposed next to the silicone layer, wherein the release layer is on the exterior.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 20C is a graph of the bending length over time of various heater coating materials at a weight of 1.2 g/si;

DETAILED DESCRIPTION

Figure 1:
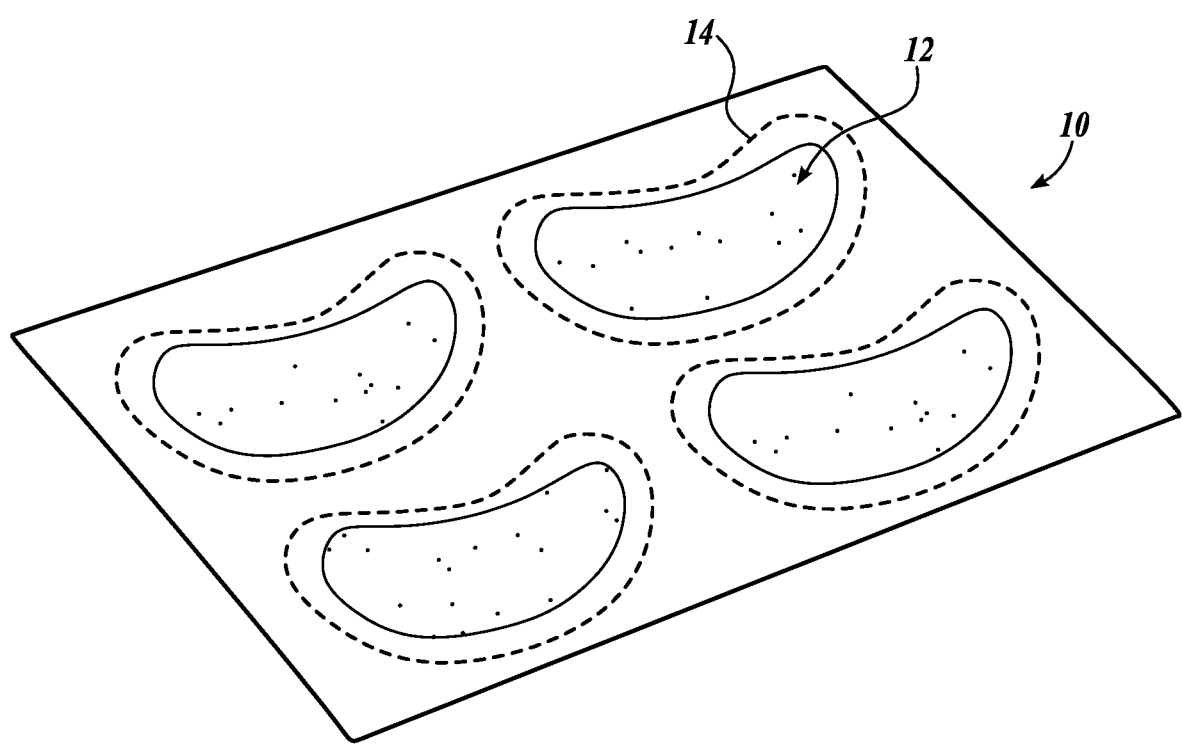
FIG. 1 is an embodiment of a package including a plurality of spot mask heaters.

Embodiments of this disclosure relate to facial masks and packages, wherein a heater can be included in the facial mask or the package. The masks have applications for applying heat to areas on the face or anywhere on the body. The heater is first activated, such as through contact with air or any exothermic chemical processes or reactions, to heat the mask, and then the mask is applied onto a skin area (with or without the heater) to be treated with heat alone and/or heat and an active component. Embodiments of this disclosure also include multiple masks in one package, where the masks are heated by one heater, such that the heater remains in the package and the mask portion is applied to the skin area to be treated.

In some embodiments, masks and packages are made by combining one or more of the layers described below. The layers can themselves be single ply or multi-ply. The layers can be glued, stitched or welded together, for example. Releasable adhesives can be used to adhere the mask onto a cover film or other layer from which the mask is removed and to adhere the mask to the skin. Masks are provided in different packaging embodiments. In one embodiment, masks are packaged on sheets. In one embodiment, single masks are packaged in individual packages. In one embodiment, multiple masks are packaged in a single package.

Layers are described below for forming the packages and the masks. Layer numbers correspond to particular uses and/or materials; however, layers having the same number among the different packages and masks can take on various shapes and forms.

Actives/Product Layer (100)

Actives in this disclosure include any one or more compounds and compositions that are applied to skin or that transfer through the skin to provide a user with a treatment. Actives include, but are not limited to, medicines, pharmaceuticals, nutraceuticals, cosmetics, micronutrients, vitamins, minerals, and the like.

Actives are present on a substrate. In one embodiment, the substrate is a hydrogel. As used herein, "hydrogel" refers to a substance formed when an organic hydrophilic polymer, (natural or synthetic) that is crosslinked via covalent, ionic, or hydrogen bonds to form a three-dimensional open-lattice network structure that entraps water molecules to form a gel. In some embodiments, hydrogels contains 90% or more water (e.g., 80% or more, 70% or more, 60% or more, or 50% or more) by volume. In one embodiment, actives are infused into hydrogels. AMGEL® infused hydrogels from Axelgaard Manufacturing are provided as representative embodiments that are infused with, for example, hyaluronic acid, collagen, honey, aloe vera, and menthol. In one embodiment, the product layer 100 is also an "adhesive" that can adhere the mask to the skin. In one embodiment, the adhesive is a hydrogel, such as AXELGAARD AG735. In one embodiment, the product layer 100 is a silicon adhesive, such as a 3M breathable silicone adhesive. In the case of the silicone adhesive, an additional adhesive is used to adhere the silicone layer to the mask. In one embodiment, to adhere a silicone layer to the mask, an acrylic adhesive is used with a thermoplastic elastomer carrier film between the acrylic adhesive and the silicone layer.

In other embodiments, the product layer may not be good at adhering to the skin. Accordingly, in such cases, an additional adhesive layer is used. Product layers made from materials that may include an additional adhesive layer, include, for example, nonwoven webs of natural or synthetic polymers. Natural polymers include cellulosic fibers.

A characteristic of the product layer 100 or an adhesive layer on the product layer 100 is the peel strength. Representative peel strengths are given in Table 1 of Example 1. Peel strength of the product layer 100 or any adhesive layer can range from 0.4 to 25 N/inch or any value in between this lower and upper limit.

In one embodiment, the thickness of the hydrogel product layer is from 0.025 to 0.045 inches. In one embodiment, the thickness of the hydrogel product layer is from 0.030 to 0.040 inches. In one embodiment, the thickness of the hydrogel product layer is about 0.035 inches.

In one embodiment, the thickness of the silicone adhesive layer is from 0.001 to 0.01 inches. In one embodiment, the thickness of the silicone adhesive layer is from 0.002 to 0.008 inches. In one embodiment, the thickness of the silicone adhesive layer is about 0.005 inches.

In one embodiment, the thickness of the carrier film layer juxtaposed next to the silicone adhesive layer is from 0.0005 to 0.005 inches. In one embodiment, the thickness of the carrier film layer is from 0.001 to 0.003 inches. In one embodiment, the thickness of the carrier film layer is about 0.0015 inches.

In one embodiment, the thickness of the acrylic adhesive layer juxtaposed next to the carrier film is from 0.0005 to 0.005 inches. In one embodiment, the thickness of the acrylic adhesive layer is from 0.001 to 0.003 inches. In one embodiment, the thickness of the acrylic adhesive layer is about 0.0017 inches.

In some embodiments, a release liner is juxtaposed next to the product layer 100 or to the adhesive layer if the product layer 100 is provided with an additional adhesive. A release liner is used to protect the product layer 100 until ready for use. In one embodiment, a release liner comprises a polyethylene film. In one embodiment, a release liner comprises a Kraft paper material. In one embodiment, the release liner comprises a polyethylene terephthalate material. The release liner is removed prior to applying the mask to the skin.

In one embodiment, the thickness of the release liner is from 0.001 to 0.010 inches. In one embodiment, the thickness of the release liner is from 0.003 to 0.007 inches. In one embodiment, the thickness of the release liner is about 0.005 inches.

Barrier Film Layer (200)

The barrier film layer 200 is for preventing the migration of air and specifically oxygen from reaching the heater layer 300 until the heater is desired to be activated. In one embodiment, the barrier film layer 200 comprises a metallized film (CELPLAST O2 sealant). In one embodiment, the barrier film layer 200 comprises a metallized low density polyethylene film. In one embodiment, the barrier film layer 200 comprises a metallized polypropylene film. In one embodiment, the barrier film layer 200 comprises a metallized polyethylene terephthalate film. In one embodiment, the barrier film layer 200 comprises a biaxially-oriented polypropylene film. In one embodiment, the barrier film layer 200 comprises a low density polyethylene film. In one embodiment, the barrier film layer 200 comprises a polyacrylic acid film.

In some embodiments, barrier film 200 is a single ply. In some embodiments, the barrier film 200 comprises multiple plys. The barrier film layer 200 can be used for multiple purposes or functions. In one embodiment, the barrier film 200 fully encloses the heater layer 300 on all sides, such as in a pouch or package. In some embodiments, a pouch or package made from barrier film 200 enclosing the heater 300 is provided with holes on one side, wherein the holes are then temporarily sealed with another layer (peel off layer) of barrier film with a releasable adhesive.

In one embodiment, the use of masks on the face requires that the films have a certain conformability. Conformability is measured by a force given a certain extensibility or by a bending length over time value. The parameters are described in Example 2. In one embodiment, the barrier film 200 layer has an extensibility of 20% at a force of less than 70,000 lbs or less than 10,000 lbs or less than 25,000 lbs, or a bending length over time value of 3 mm to 65 mm at 10 mins.

In one embodiment, the thickness of the barrier film layer 200 is from 0.0001 to 0.010 inches. In one embodiment, the thickness of the barrier film layer 200 is from 0.0005 to 0.007 inches. In one embodiment, the thickness of the barrier film layer 200 is about 0.0015 inches.

Heater (300)

In one embodiment, a heater is comprised of a metal-air battery. In one embodiment, a heater is comprised of a zinc-air battery (ZAB). A zinc-air battery provides a thin flexible and wearable source of heat for wearable face masks and skin patches of this disclosure. One embodiment of a zinc-air battery works by adsorbing oxygen from the surrounding air into one layer of the zinc-air battery. Then, the oxygen is reduced with a reduction catalyst at the air electrode (cathode). The construction and operation of many zinc-air batteries is known. However, while the present disclosure uses zinc-air batteries, the selection criteria of a suitable zinc-air battery is based on particular selection criteria, such as the ability to conform to soft tissues on the face and other body parts.

In other embodiments of a heater, chemical components that produce an exothermic process or reaction can be used as a source of heat. Other exothermic processes or reactions that can be used to generate heat include the use of calcium chloride, calcium nitrate, other alkaline earth metals, and the like.

In one embodiment, the thickness of the heater layer 300 is from 0.020 to 0.040 inches. In one embodiment, the thickness of the heater layer 300 is from 0.025 to 0.035 inches. In one embodiment, the thickness of the heater layer 300 is about 0.030 inches.

Substrate Layer (400)

The substrate layer 400 is provided to allow air and oxygen to reach the heater 300. In one embodiment, the substrate layer 400 is a micro-cavitated low density polyethylene. For example, the substrate layer is a breathable film provided from Clopay Corporation. In one embodiment, the air breathable film is biaxially-oriented polypropylene, low density polyethylene, polyacrylic acid or a combination.

In one embodiment, the substrate 400 layer has an extensibility of 20% at a force of less than 70,000 lbs or less than 10,000 lbs or less than 25,000 lbs, or a bending length over time value of 3 mm to 65 mm at 10 mins.

In one embodiment, the thickness of the substrate layer 400 is from 0.0001 to 0.0015 inches. In one embodiment, the thickness of the substrate layer 400 is from 0.003 to 0.001 inches. In one embodiment, the thickness of the substrate layer 400 is about 0.0008 inches.

Film with Holes Layer (500)

The film with holes layer 500 is the same material and thickness as the film barrier layer 200. In one embodiment, the film with holes 500 layer has an extensibility of 20% at a force of less than 70,000 lbs or less than 10,000 lbs or less than 25,000 lbs, or a bending length over time value of 3 mm to 65 mm at 10 mins.

Peel Off Film/Cover Film Layer (600)

In some embodiments, the peel off/cover film layer 600 is the same material as the barrier film layer 200 in order to prevent air and oxygen from reaching the film with holes layer 500. In some embodiments, the peel off film layer 600 is provided with a releasable adhesive that releasably attaches the peel off film layer 600 to the film with holes layer 500. When functioning as a cover film layer, in some embodiments the cover film layer can be molded, such as by heat or vacuum or both heat and vacuum. Thermoformable plastics can be heated and molded into trays, for example.

In one embodiment, the peel off film/cover film 600 layer has an extensibility of 20% at a force of less than 70,000 lbs or less than 10,000 lbs or less than 25,000 lbs, or a bending length over time value of 3 mm to 65 mm at 10 mins.

Cardstock (800)

Cardstock layer 800 is a material that is used for its heat resistant properties and that can resist deformation at the elevated temperatures at the temperature ranges produced from the heater 300. Cardstock 800 layer may be a single ply or multiple plys. Cardstock may be made from nonwoven fibers. Fibers can include natural and synthetic fibers. Natural fibers include cellulose. Cardstock can include pulp and paper products, bleached or unbleached.

The Packages

The above described films and material layers are used in assembling packages. Packages are made to include the heater masks in an inactive state and prevent their activation until a user activates the heater prior to use. In one embodiment, heater masks are kept in an inactive state by preventing air from reaching into and reacting with the heater layer of a mask or package. When the user activates the heater, such as by allowing air to come in contact with the heater, the heater has a predetermined life during which heat is generated. In some embodiments, a package contains a single heater mask. In some embodiments, a package contains a plurality of masks and a single heater. Packages are formed from the above described material/functional layers. Some layers are designed to peel away from juxtaposed layers or are not attached in any manner to a juxtaposed layer. Multiple layers intended to remain together as a unit can be stitched, welded, or more permanently adhered together. The same layer designation in a different package represents a similar function and/or material layer being used in the different package.

Figure 2:
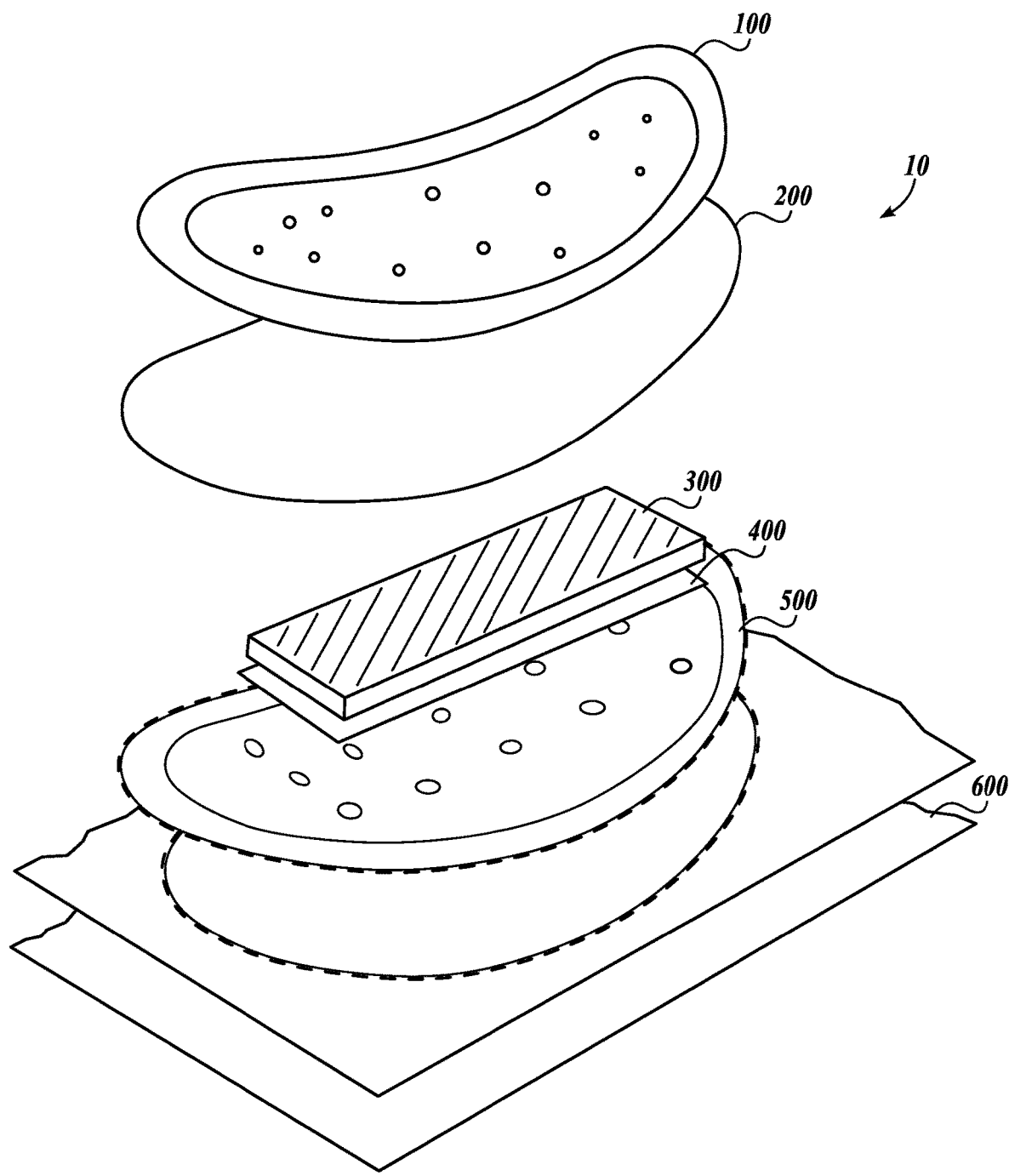
FIG. 2 is the exploded view of the package of FIG. 1 showing the various layers.

Referring to FIGS. 1 and 2, the package 10 is provided as a multi-layer sheet product from which the heater masks 12 can be peeled from the cover film layer 600. The cover film layer 600 is made from an air-impermeable material to prevent air from reaching the heater layer 300. The cover film layer 600 is adhered to the masks 12. When a mask 12 is peeled off, air is allowed to contact and react with the heater layer 300 to produce heat.

Referring to FIG. 2, the package 10 is comprised of the following layers in the following order. The actives/product layer 100 is on the exterior. The barrier film layer 200 is juxtaposed below the actives/product layer 100. The heater layer 300 is juxtaposed below the barrier film layer 200. The substrate layer 400 is juxtaposed below the heater layer 300. The film with holes layer 500 is juxtaposed below the substrate layer 400. The cover film layer 600 is juxtaposed below the film with holes layer 500. A releasable adhesive is used between the cover film layer 600 to attach to the film with holes layer 500. In this embodiment, the layers 100 and 200 are provided in the shape of the mask, and the layers 300 and 400 are provided in a rectangular shape that are included within the boundaries of the mask. In this embodiment, the mask 12 that is placed on the skin includes the layers 100, 200, 300, 400, and 500, which are intended to remain as a unit. The layer 500 is coextensive with the cover film layer 600; however, the layer 500 is pre-scored to tear along the scoring line 14 in the shape of the mask 12 to allow lifting the mask 12 from the cover film layer 600.

Figure 3:
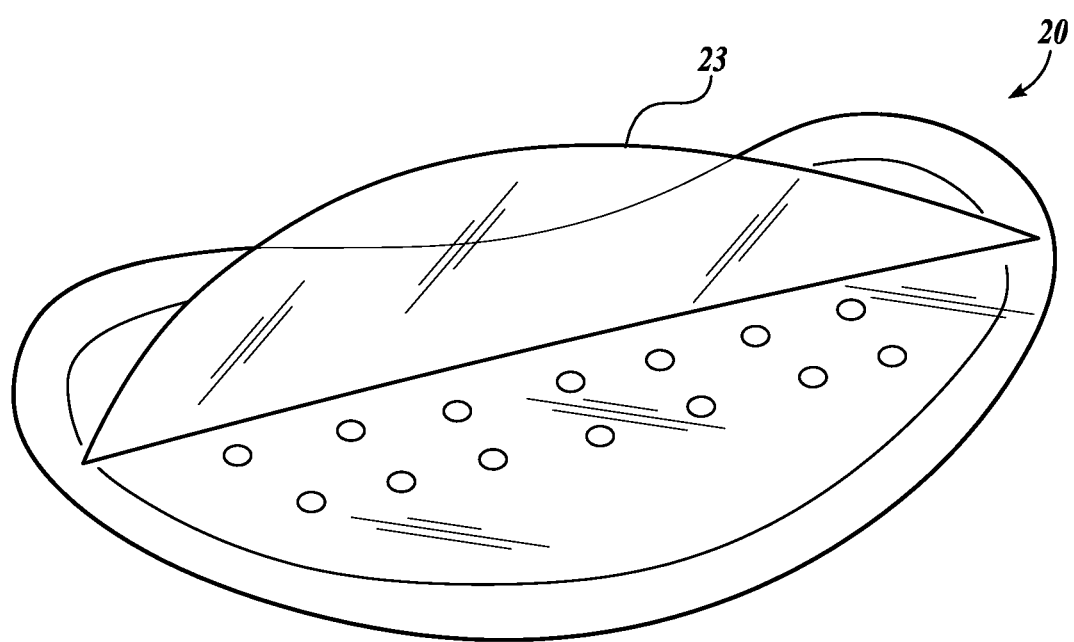
FIG. 3 is an embodiment of a package including a spot mask heater.
Figure 4:
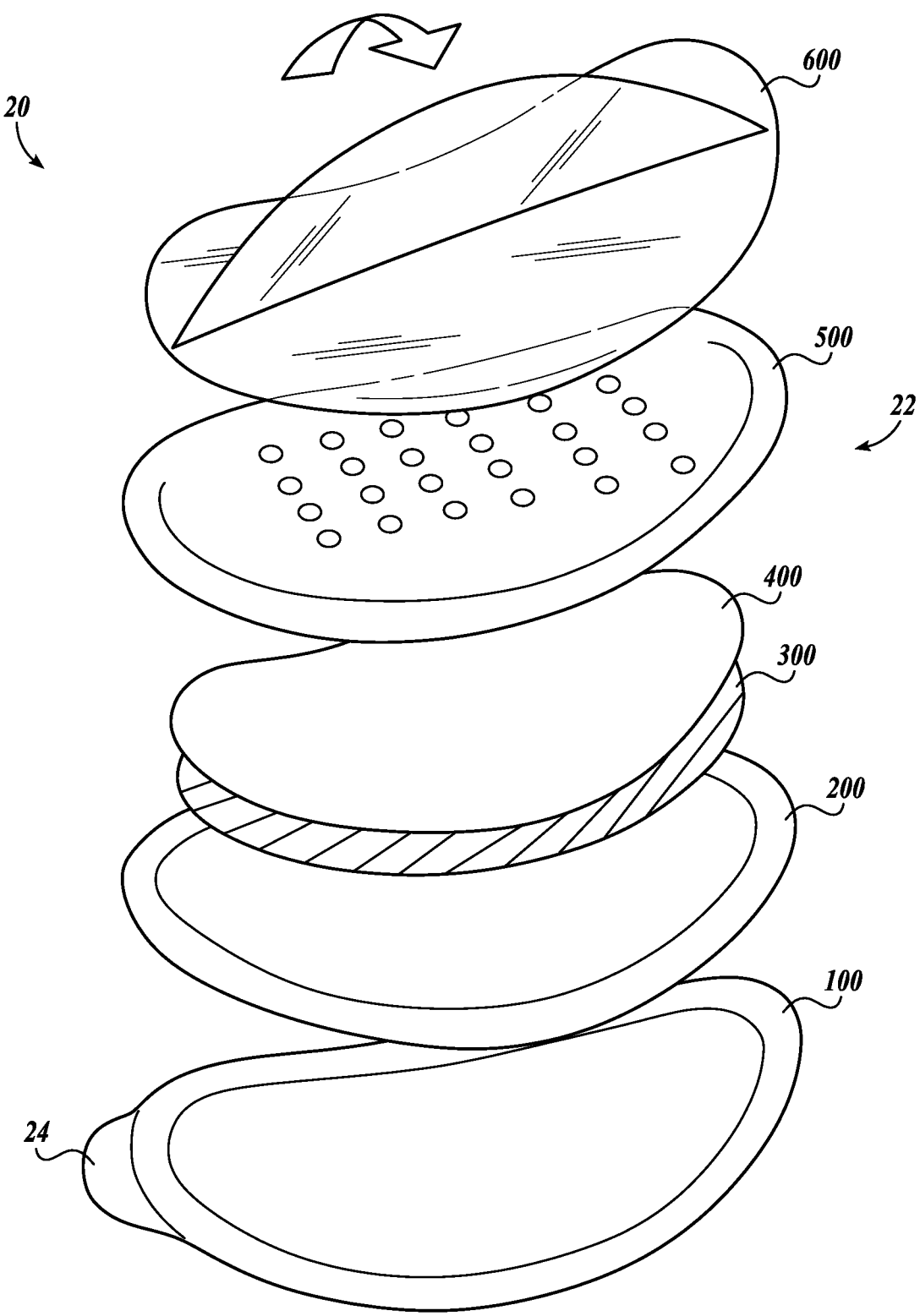
FIG. 4 is the exploded view of the package of FIG. 3 showing the various layers.

Referring to FIGS. 3 and 4, the package 20 includes a single mask. The package 20 includes a peel off film layer 600 with a tab 23 for grasping and pulling off the peel off film layer 600 to activate the heater 300. The peel off film layer 600 is made from an air-impermeable material to prevent air from reaching the heater.

Referring to FIG. 4, the package 20 is comprised of the following layers in the following order. The actives/product layer 100 is on the exterior bottom. The actives/product layer 100 includes a second grasping tab 24 to counteract the pulling force from the peel off film tab 23 of the peel off film layer 600. The barrier film layer 200 is juxtaposed above the actives/product layer 100. The heater layer 300 is juxtaposed above the barrier film layer 200. The substrate layer 400 is juxtaposed above the heater layer 300. The film with holes layer 500 is juxtaposed above the substrate layer 400. The peel off film layer 600 is juxtaposed above the film with holes layer 500. A releasable adhesive is used between the peel off film layer 600 and the film with holes layer 500. In this embodiment, the layers 100, 200, 300, 400, 500, and 600 are provided in the shape of the mask, and are the layers intended to remain as a unit mask that is placed on the skin.

Figure 5:
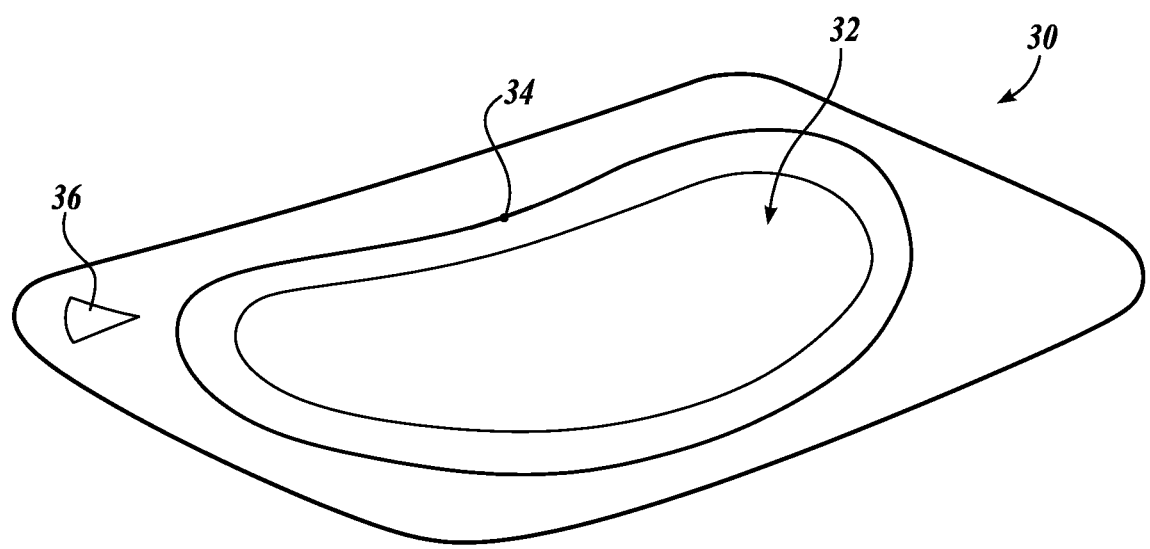
FIG. 5 is an embodiment of a package including a spot mask heater.
Figure 6:
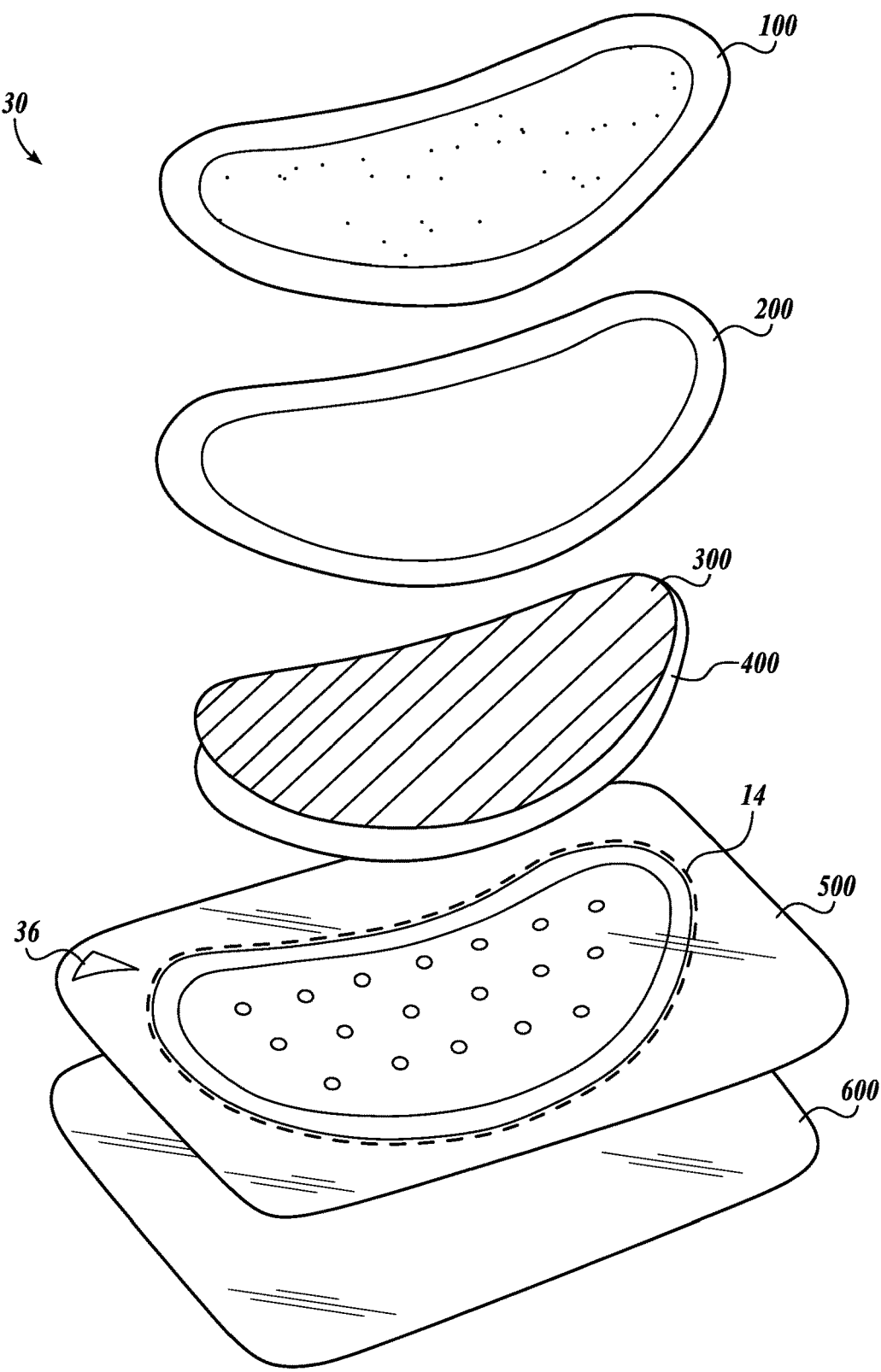
FIG. 6 is the exploded view of the package of FIG. 5 showing the various layers.

Referring to FIGS. 5 and 6, the package 30 includes a single mask. The package 30 is provided as a multi-layer sheet product from which a single heater mask 32 can be peeled from an underlying film cover layer 600. The file cover layer 600 includes a tab 36 with indicator for grasping to enable pulling off the mask. The film cover layer 600 is made from an air-impermeable material to prevent air from reaching the heater. The film cover layer 600 is adhered to the juxtaposed layer of the mask 32. When the mask 32 is peeled off, air is allowed to contact and react with the heater layer 300 to produce heat.

Referring to FIG. 6, the package 30 is comprised of the following layers in the following order. The actives/product layer 100 is on the top exterior. The barrier film layer 200 is juxtaposed below the actives/product layer 100. The heater layer 300 is juxtaposed below the barrier film layer 200. The substrate layer 400 is juxtaposed below the heater layer 300. The film with holes layer 500 is juxtaposed below the substrate layer 400. The cover film layer 600 is juxtaposed below the film with holes layer 500. A releasable adhesive is used between the cover film layer 600 to attach to the film with holes layer 500. In this embodiment, the layers 100, 200, 300, 400 are provided in the shape of the mask, and the layers 500 and 600 are coextensive and provided in a rectangular shape that extend beyond the boundaries of the mask. The layer 500 is provided with a tab 36 and indicator to show the place where the adhesive to the mask is weakened to begin peeling. In this embodiment, the mask 12 that is placed on the skin includes the layers 100, 200, 300, 400, and 500, which are intended to remain as a unit. The layer 500 is pre-scored to tear along the scoring line 14 to allow lifting the mask 12 from the cover film layer 600.

Figure 7:
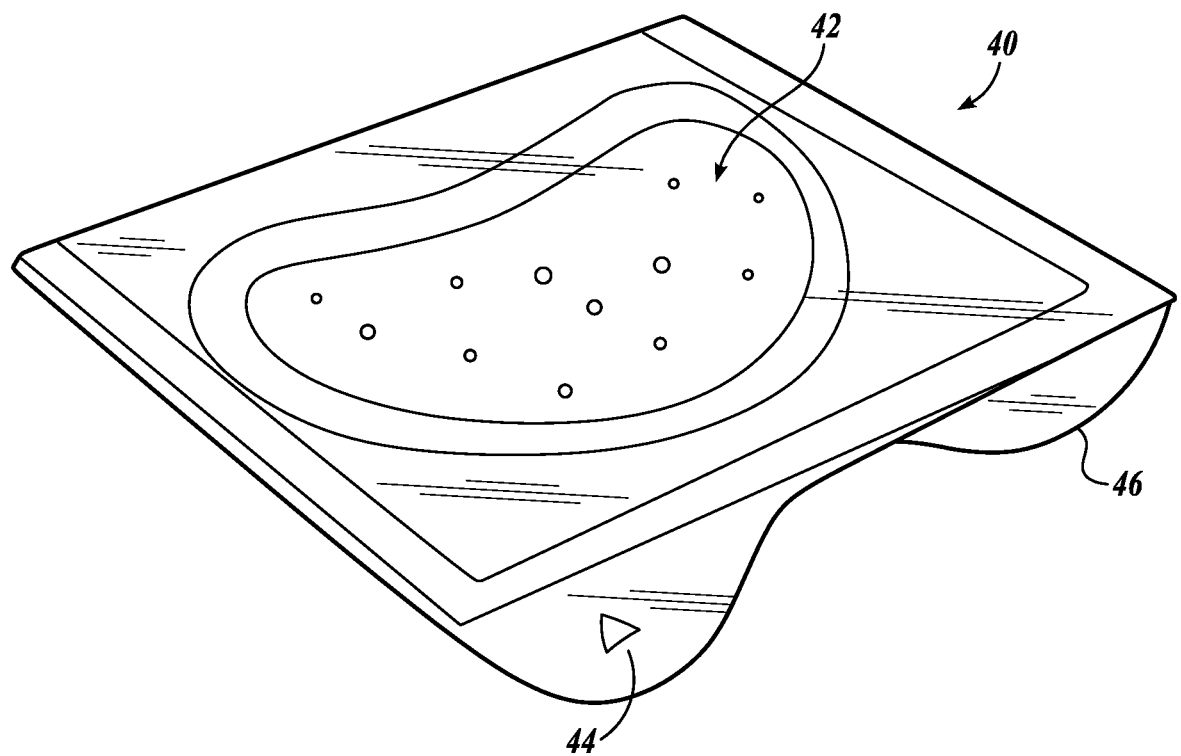
FIG. 7 is an embodiment of a package including a spot mask heater.
Figure 8:
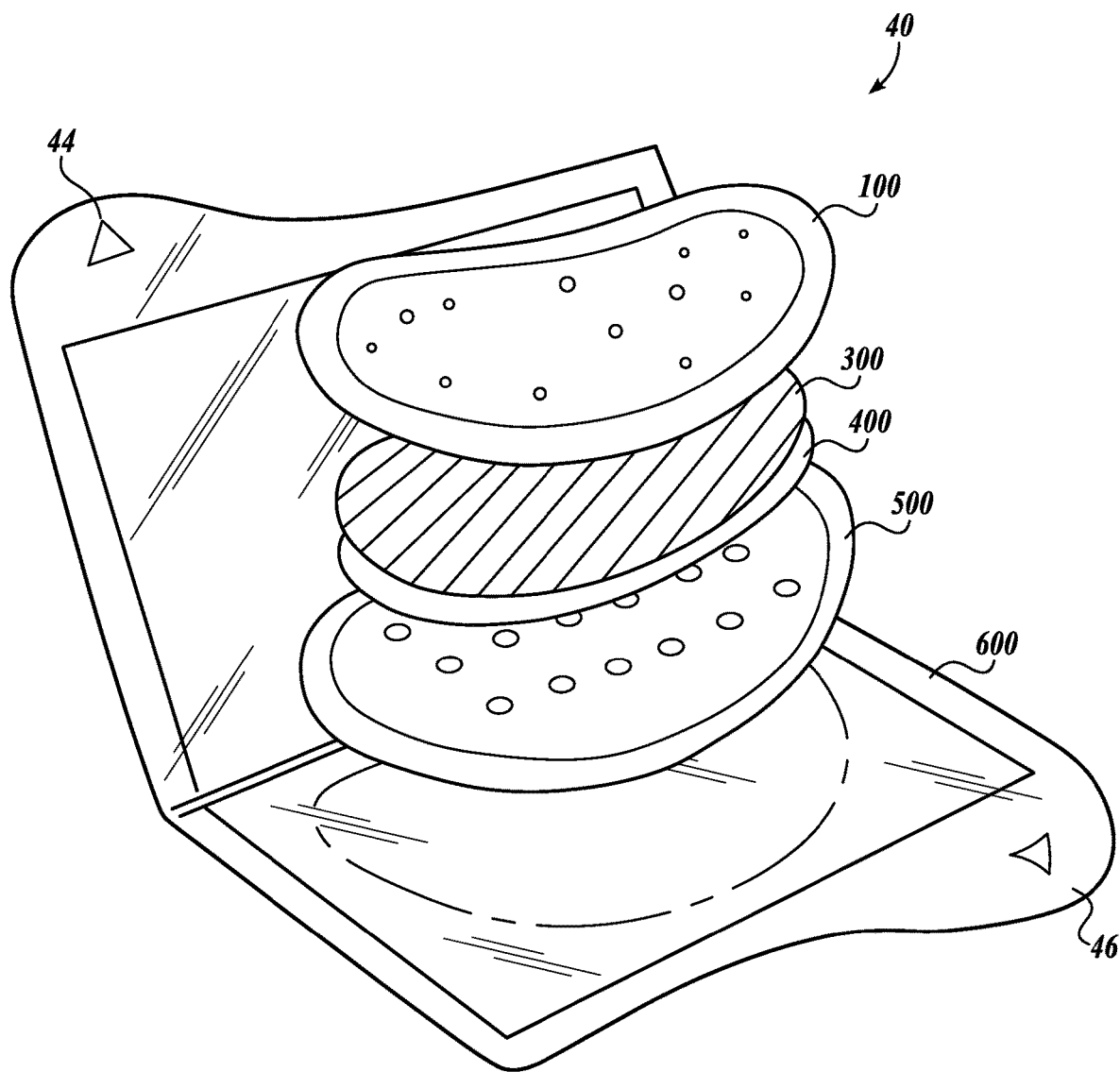
FIG. 8 is the exploded view of the package of FIG. 7 showing the various layers.

Referring to FIGS. 7 and 8, the package 40 includes a single mask. The package 40 is provided with a cover film 600 envelope sealing the mask 42 from above and below the mask 42 as well as from the sides. The cover film 600 envelope is made from an air-impermeable material to prevent air from reaching the heater. In this embodiment, the mask need not be adhered to the cover film 600 envelope, because the cover film 600 envelope entirely seals the mask 42 from all sides to prevent air intrusion. The upper and lower halves of the cover film 600 envelope, however, can be adhered to each other on three sides. An upper grasping tab 44 on the upper half and a lower grasping tab 46 on the lower half allow a user to pull the two halves of the cover film 600 envelope apart thereby allowing air to contact and react with the heater layer 300 of the mask 42.

Referring to FIG. 8, the package 40 is comprised of the following layers in the following order. The upper half of the cover film 600 envelope is on the exterior. The actives/product layer 100 is juxtaposed below the upper half of the cover film 600 envelope. There is no barrier film layer 200 in this embodiment. The heater layer 300 is juxtaposed below the actives/product layer 100. The substrate layer 400 is juxtaposed below the heater layer 300. The film with holes layer 500 is juxtaposed below the substrate layer 400. The lower half of the cover film 600 envelope is juxtaposed below the film with holes layer 500. In this embodiment, the layers 100, 300, 400, and 500 are provided in the shape of the mask, and the cover film 600 is provided as the exterior upper and lower halves of an envelope that is sized to accommodate the mask on the inside. In this embodiment, the mask 12 that is placed on the skin includes the layers 100, 300, 400, and 500, which are intended to remain as a unit.

Figure 9:
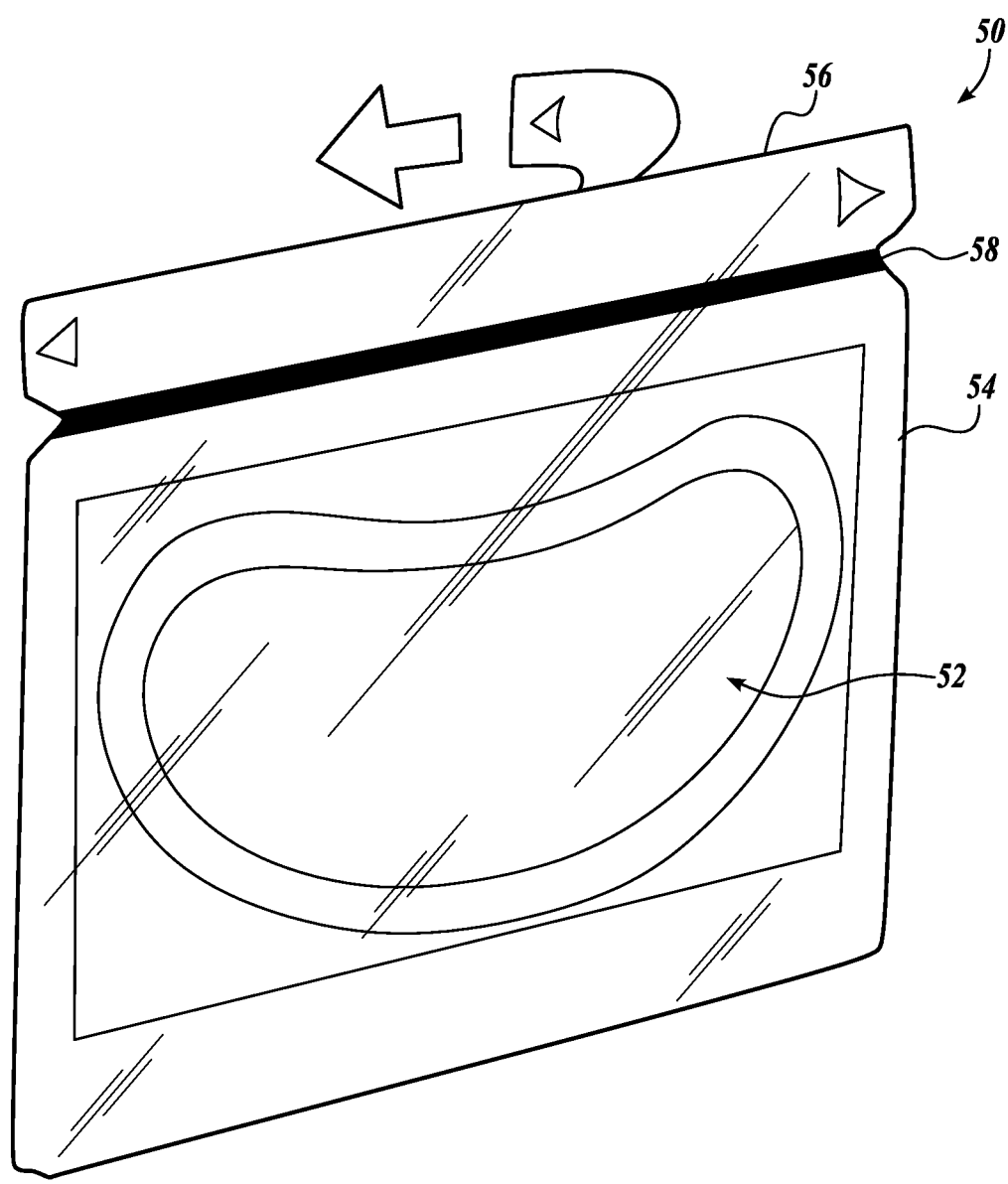
FIG. 9 is an embodiment of a package including a spot mask heater.
Figure 10:
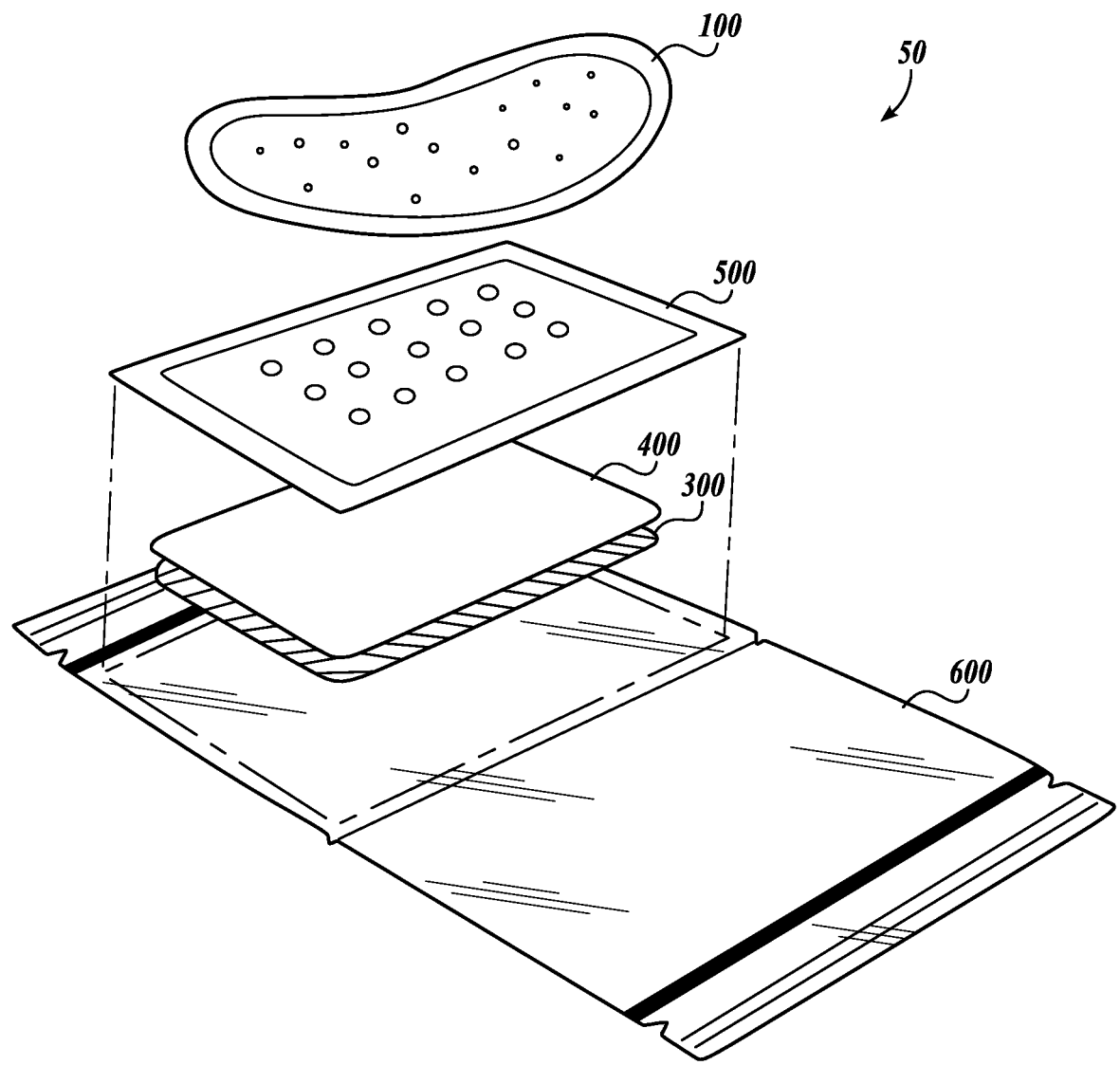
FIG. 10 is the exploded view of the package of FIG. 9 showing the various layers.

Referring to FIGS. 9 and 10, the package 50 includes a single mask. The package 50 is provided with a cover film 600 pouch 54 containing the mask 52. The cover film pouch 54 is made from an air-impermeable material to prevent air from reaching the heater. The cover film pouch 54 can be a material that is doubled over on itself, and then the first and second halves are sealed by welding on three sides. In this embodiment, the mask 52 need not be adhered to the cover film pouch 54, because the cover film pouch 54 entirely seals the mask 52 to prevent air intrusion. The cover film pouch 54 includes a single open side that is first sealed with a resealable ziplock strip 58. The cover film pouch 54 includes a second single-use security strip 56 to further seal the one open side of the cover film pouch 54, in addition to the ziplock strip 58. To activate the heater 300, the single-use security strip 56 is first torn off, then, the cover film pouch 54 is opened at the ziplock strip 54 to allow air to contact and react with the heater layer 300 of the mask 52. In one embodiment, after the security strip 56 is torn off, the user does not have to open the ziplock strip 58, and therefore can wait for a period before activating the heater 300. However, the ziplock strip 58 may not be perfectly air impermeable, therefore, the user may not delay indefinitely. Furthermore, after removing and using the heater mask 52 for a first time, the user may store the mask 52 in the cover film pouch 54 and reseal the film pouch with the ziplock strip 58 thereby slowing down the reaction and extending the life of the heater 300 to use at another time.

Referring to FIG. 10, the package 50 is comprised of the following layers in the following order. The lower half of the cover film 600 pouch is on the exterior. The heater layer 300 is juxtaposed above the lower half of the cover film 600 pouch. The substrate layer 400 is juxtaposed above the heater layer 300. The film with holes layer 500 is juxtaposed above the substrate layer 400. The actives/product layer 100 is juxtaposed above the film with holes layer 500. The upper half of the cover film 600 pouch is juxtaposed above the actives/product layer 100. In this embodiment, only the actives/product layer 100 is in the shape of the mask. The layers 300, 400, and 500 are provided in the shape of a rectangle that extends beyond the boundaries of the layer 100. In this embodiment, after the pouch is opened to activate the heater, the actives/product layer 100 is removed to be used as the mask that is placed on the skin.

Figure 11:
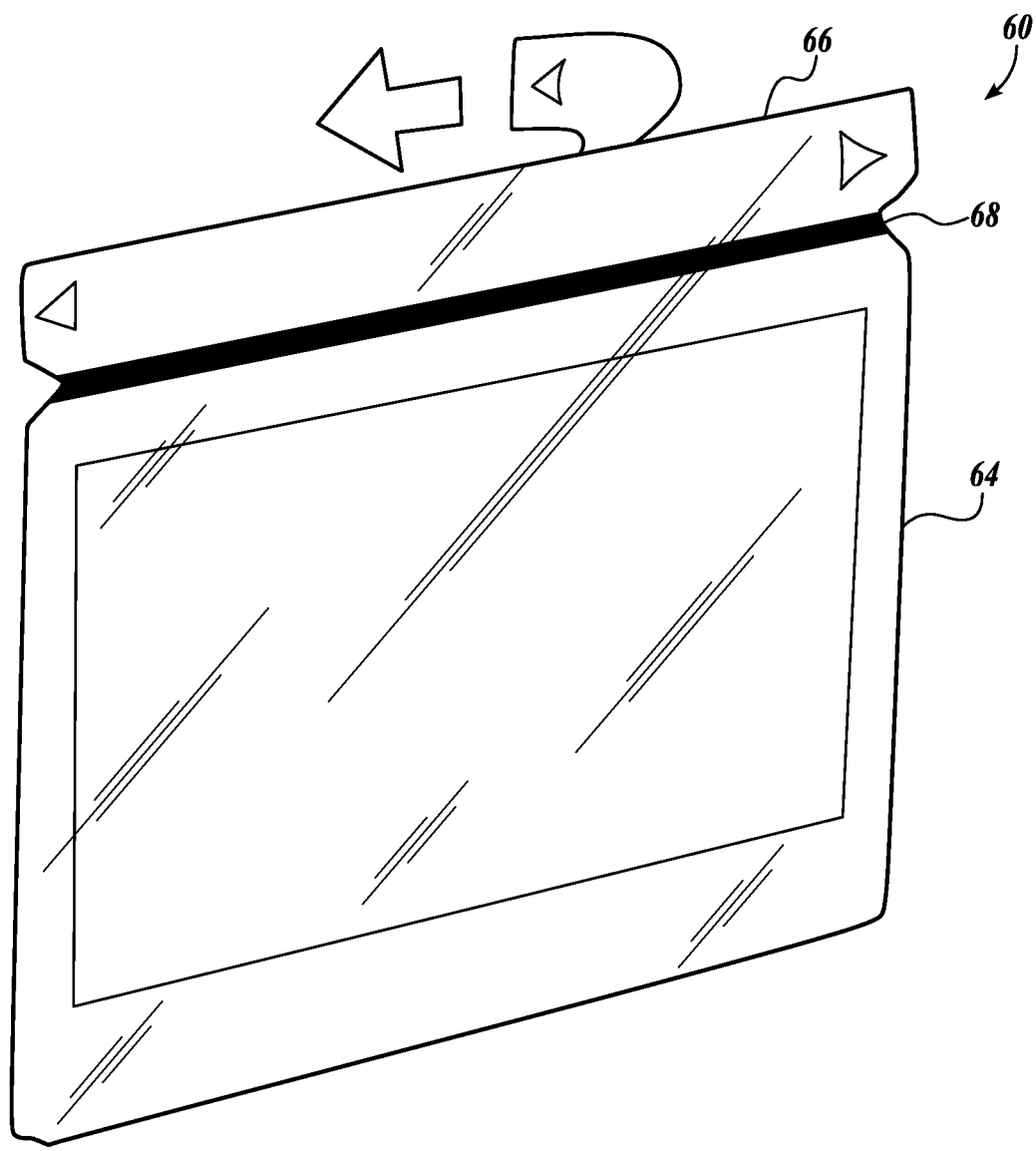
FIG. 11 is an embodiment of a package including a spot mask heater.
Figure 12:
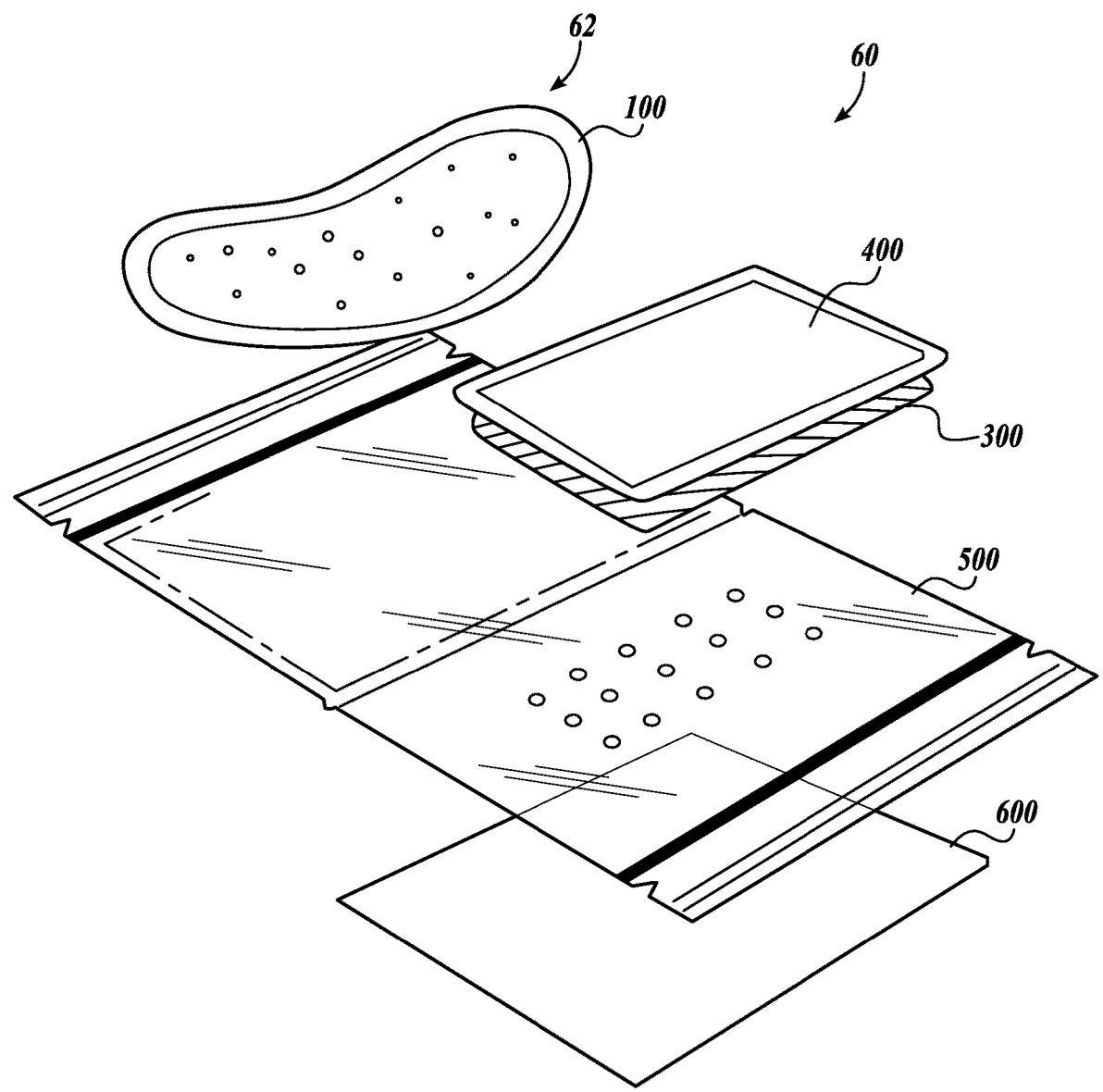
FIG. 12 is the exploded view of the package of FIG. 11 showing the various layers.

Referring to FIGS. 11 and 12, the package 60 includes a single mask. The package 60 is provided with a film with holes 500 pouch 64 containing the mask. The film with holes pouch 64 is made from an air-impermeable material to prevent air from reaching the heater 300. The film with holes pouch 64 can be a material that is doubled over on itself, and then the first and second halves are sealed by welding on three sides. In this embodiment, the mask need not be adhered to the film with holes pouch 64, because the film with holes pouch 64 entirely seals the mask and heater to prevent air intrusion. The film with holes pouch 64 includes a single open side that is first sealed with a resealable ziplock strip 68. The film with holes pouch 64 includes a second single-use security strip 66 to further seal the one open side of the film with holes pouch 64, in addition to the ziplock strip 68. The lower half of the film with holes pouch 64 has the holes, which are temporarily sealed with a peel off film 600. To activate the heater 300, the peel off film 600 is peeled from the film with holes 500 to allow air entry into the pouch 64. A waiting period can be allowed. After a predetermined period for heating, the single-use security strip 66 can be torn off, then, the film with holes pouch 64 is opened at the ziplock strip 54 to remove the mask.

Referring to FIG. 12, the package 60 is comprised of the following layers in the following order. The exterior bottom layer is the peel off film layer 600. The lower half of pouch 64 is a film with holes layer 500 that is juxtaposed above the peel off film layer 600. The heater layer 300 is juxtaposed above the film with holes layer 500. The substrate layer 400 is juxtaposed above the heater layer 300. The actives/product layer 100 is juxtaposed above the substrate layer 400. The upper half of the pouch 64 is an extension of the film with holes layer 500 and is juxtaposed above the actives/product layer 100. In this embodiment, only the actives/product layer 100 is in the shape of the mask. The layers 300, 400, and 500 are provided in the shape of a rectangle that extends beyond the boundaries of the layer 100. In this embodiment, after the pouch 64 is opened, the actives/product layer 100 is removed to be used as the mask that is placed on the skin.

Figure 13:
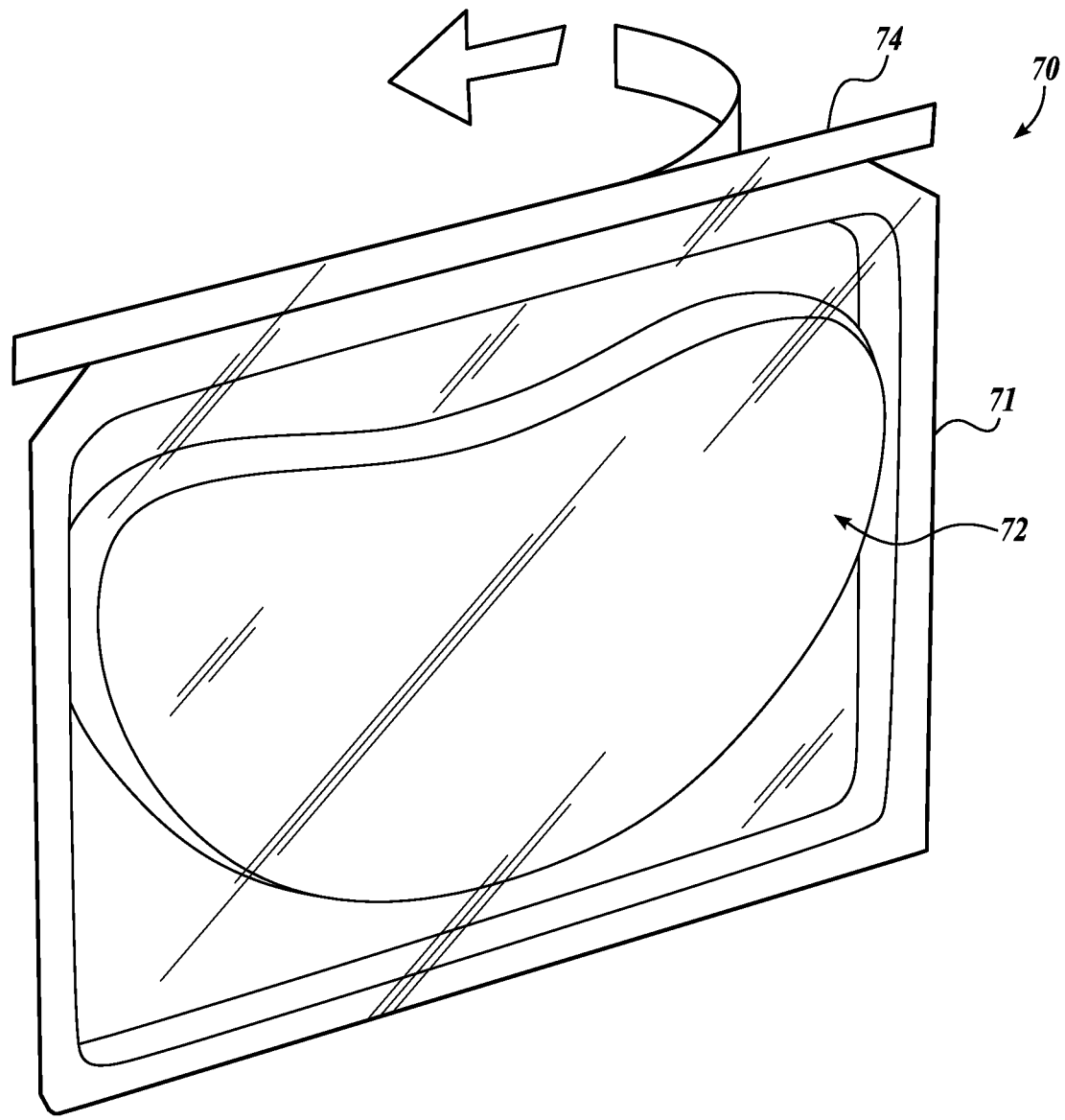
FIG. 13 is an embodiment of a package including a spot mask heater.

Referring to FIG. 13, the package 70 holds a single mask 72. The package 70 is provided as a tray 71 for holding a single heater and one mask 72 at a time. The tray 71 seals the heater and mask 72 from above and below the mask 72 as well as from the sides. The tray 71 is made from an air-impermeable material to prevent air from reaching the heater. In this embodiment, the tray 71 entirely seals the mask 72 from all sides within a pocket to prevent air intrusion. In one embodiment, the tray 71 includes a first and second half joined to each other on one side that acts as a hinge. In one embodiment, the tray 71 includes a depressed pocket 73 in the shape of the mask 71 in the first half for placing the mask 72 and a second depressed pocket 75 in the shape of the heater 300 in the second half for placing the heater 300. In one embodiment, the first half includes a raised positive surface 76 for the depressed pocket 73, and the second half includes a recessed negative surface 77 for the further recessed pocket 75. Furthermore, flanges 78, 79 extend around the periphery of the raised positive 76 and recessed negative 77 surfaces so that when the first and second halves are brought together, the first half positive surface 76 will fit into the second half negative surface 77 and the flange 78 around the first half will press against the flange 79 of the second half. The first and second halves of the tray 71 fit snuggly together and may also have a resealable adhesive on the flanges, for example, to prevent the intrusion of air into the interior of the tray 71. Initially, the side of the tray 71 that is opposite from the hinge can include a single use security strip 74 that is pulled off before the first use. After the security strip 74 is pulled off, the first and second halves can be separated to activate the heater 300 and then closed again to heat the mask 72. After the first mask 72 is used, the user can place a second mask into the tray 71 to heat and then use the second mask, and thereafter, any additional mask as long as the heater 300 is producing heat. The tray 71 may be closed to extend the life of the heater 300 and opened again to re-activate the heater 300.

Figure 14:
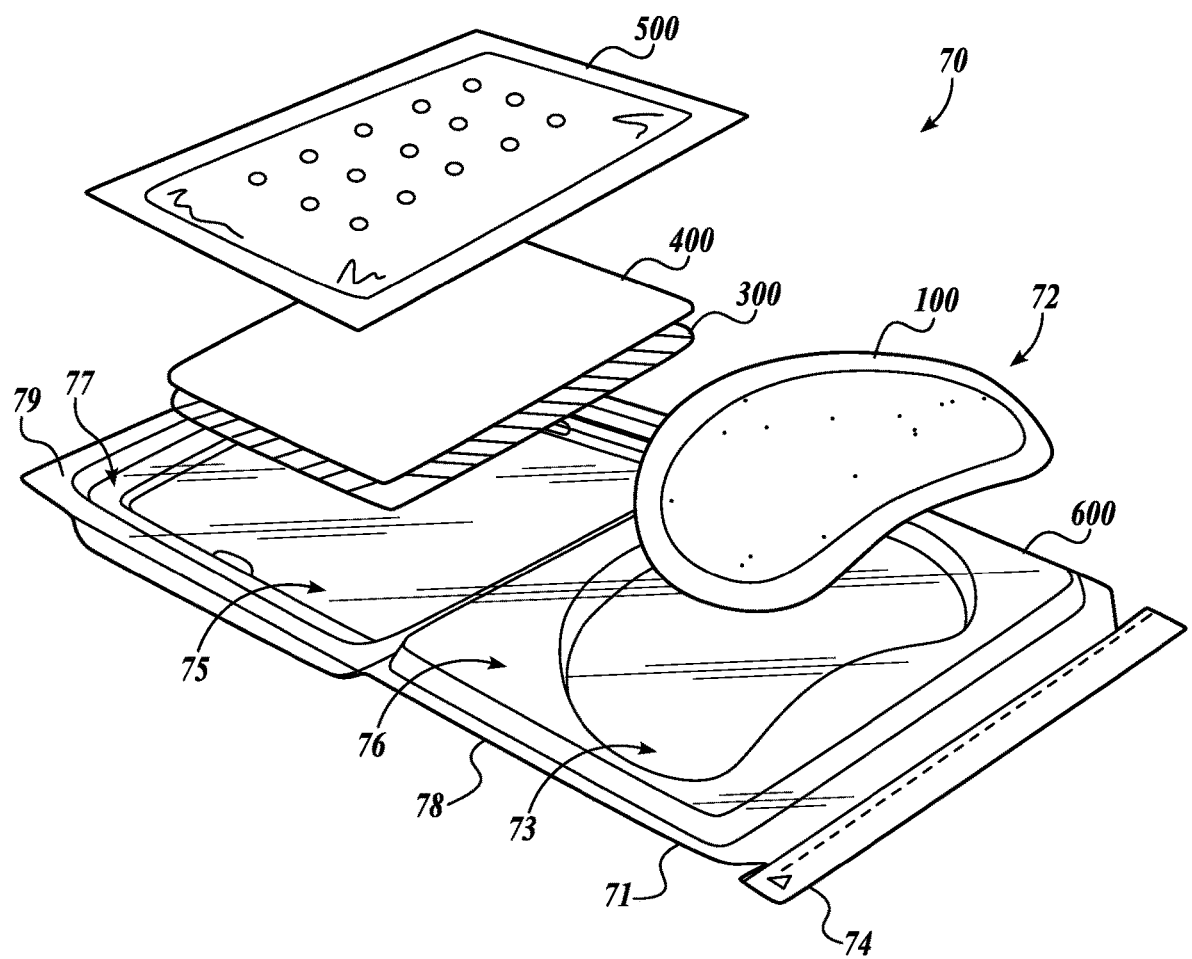
FIG. 14 is the exploded view of the package of FIG. 13 showing the various layers.

Referring to FIG. 14, the package 70 is comprised of the following layers in the following order. The lower half of tray 71 is a cover film layer 600. The actives/product layer 100 is juxtaposed above the cover film layer 600 and resides in the pocket 73. The heater layer 300 is juxtaposed above the actives/product layer 100. The substrate layer 400 is juxtaposed above the heater layer 300. The film with holes layer 500 is juxtaposed above the substrate layer 400. The upper half of the tray 71 is an extension of the cover film layer 600. In this embodiment, only the actives/product layer 100 is in the shape of the mask. The layers 300, 400, and 500 are provided in the shape of a rectangle that extends beyond the boundaries of the layer 100, and the layers 300, 400, and 500 fit into the recessed pocket 75. In this embodiment, after the tray 71 is opened, the actives/product layer 100 is removed to be used as the mask that is placed on the skin.

Figure 15:
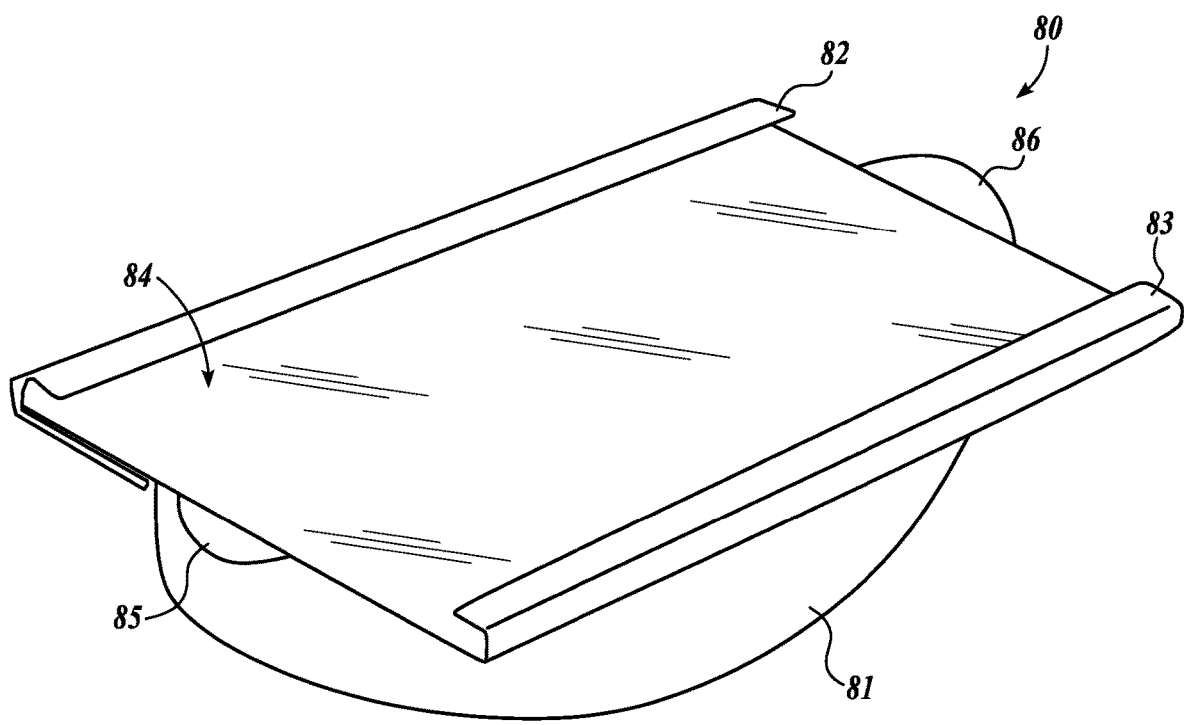
FIG. 15 is an embodiment of a package including a plurality of spot mask heaters.
Figure 16:
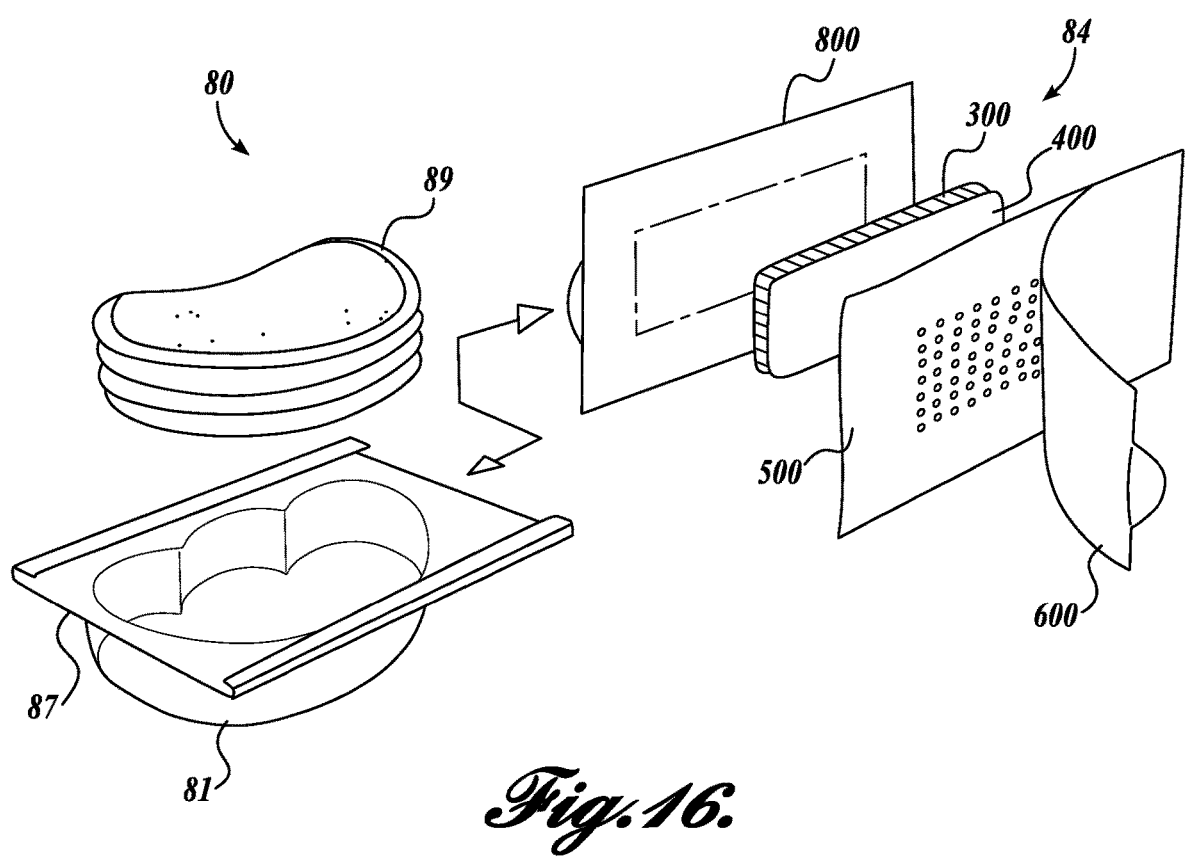
FIG. 16 is the exploded view of the package of FIG. 15 showing the various layers.

Referring to FIGS. 15 and 16, the package 80 holds multiple masks and a single heater. The package 80 is provided as a deep tray 81 container holding multiple stacked masks 89 and a single heater for the stack of masks. The tray 81 has an opening on the upper end thereof, and the tray 81 has horizontally extending edge 87 around the entire periphery of the tray opening. A first 82 and second 83 straight guideway for a sliding heater assembly 84 is provided on two opposite sides of the tray 81 by bending the horizontal edge 87 up and inward. The sliding heater assembly 84 has a first 85 and second 86 grasping tab for pulling the heater assembly 84 out and for peeling the cover film layer 600 off the heater assembly 84 exposing a film with holes layer 500 that allows air intrusion into the heater 300. The heater assembly 84 is more fully described with reference to FIG. 16. After activating the heater assembly 84, the heater assembly 84 is placed back on the tray 81 while engaging with the guideways 82, 83. The heater assembly 84 will then provide heat to heating the plurality of masks 89 in the tray 81. A user can remove one mask 89 at a time, while replacing the heater assembly 84 to the tray 81 after taking out and using each mask. The masks 89 include at least a product layer 100.

Referring to FIG. 16, the package 80 is comprised of the tray 81, a stack of masks 87, and heater assembly 84. The package 80 is assembled in the following manner. The tray 81 is formed from a cover film layer 600 for preventing intrusion of air. The stack of masks 87 is juxtaposed inside and above the bottom of the cover film layer 600. Each mask comprises an actives/product layer 100. The heater assembly 84 is juxtaposed above the stack of masks 87. The heater assembly 84 includes the following layers in the following order. The cardstock layer 800 is on the exterior upper side of the heater assembly 84. The heater 300 is juxtaposed below the cardstock layer 800. The substrate layer 400 is juxtaposed below the substrate layer 400. The film with holes layer 500 is juxtaposed below the substrate layer 400. The peel off film layer 600 is juxtaposed below the film with holes layer 500. The heater assembly 84 includes the layers 800, 300, 400, 500, and 600. However, when the peel off film layer 600 is removed to activate the heater 300, the heater assembly 84 that is placed onto the tray 81 has the layers 800, 300, 400, and 500.

Figure 17:
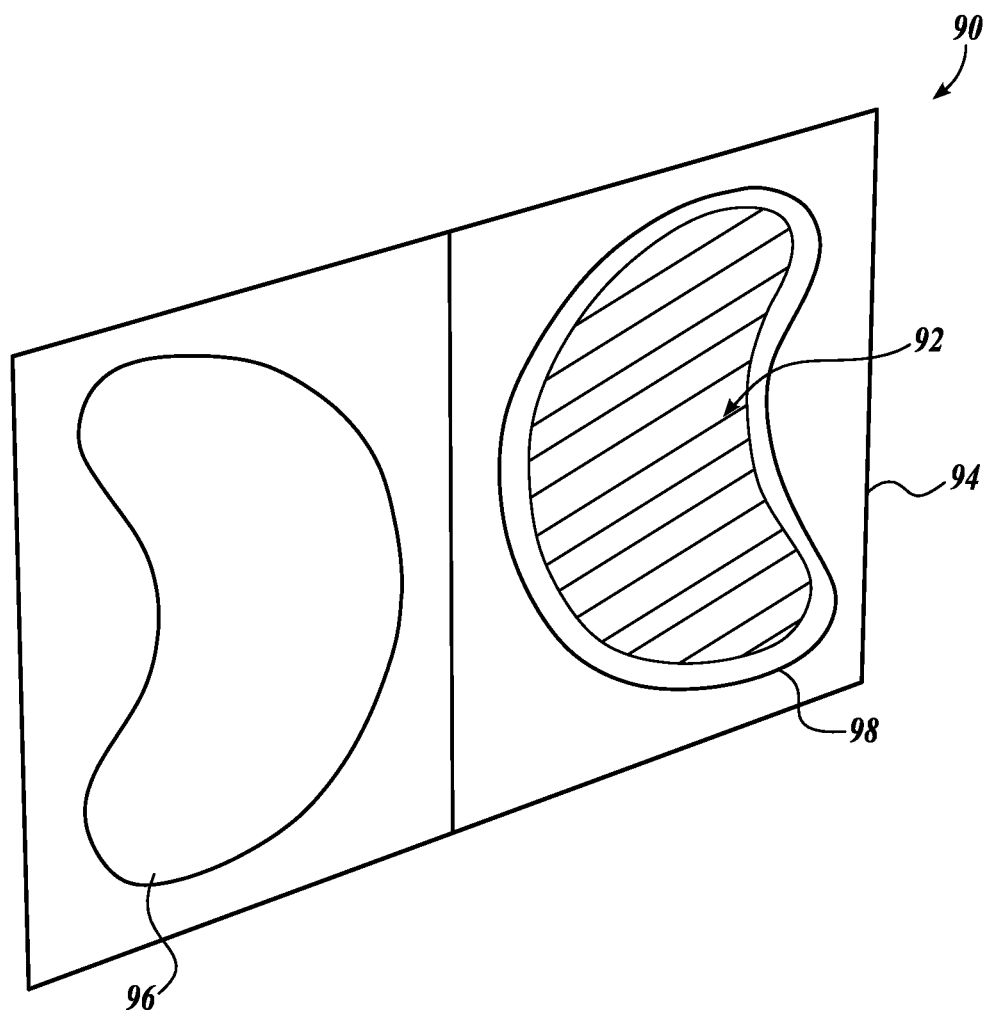
FIG. 17 is an embodiment of a package including a spot mask heater.
Figure 18:
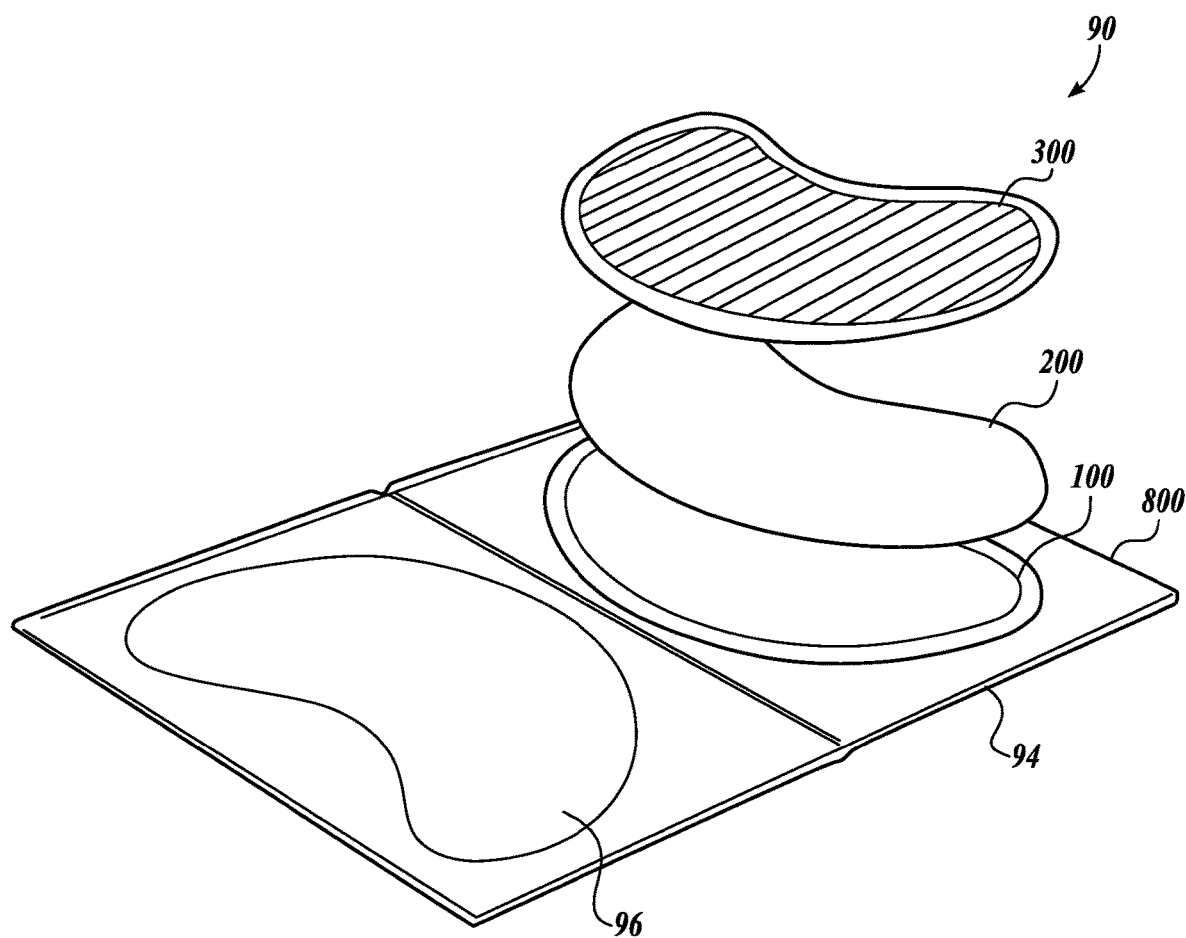
FIG. 18 is the exploded view of the package of FIG. 17 showing the various layers.

Referring to FIGS. 17 and 18, the package 90 includes a single mask. The package 90 includes a heat resistant card 94 with a crease in the middle to allow the cart to fold in half. One half of the card 94 has the mask 92 adhered to the card 94 with an inactive heater exposed on the surface. The second half of the card 94 includes a hydrogel heat activator 96. When the halves of the card 94 are brought together, the hydrogel heat activator 96 contacts the mask 92 and causes a reaction in the heater 300 to generate heat. The heater 300 layer can include any chemical that causes an exothermic process with water in the hydrogel heat activator 96, including calcium chloride, calcium nitrate, calcium oxide or any other alkaline earth metal. After a sufficient period of time, which can be indicated by a change in state or color, the card 94 is reopened, and the mask 92 is removed from the card 94 along the pre-scored line 98.

Referring to FIG. 18, the package 90 is comprised of the following layers in the following order. The cardstock layer 800 forms both halves of the card 94. The actives/product layer 100 is juxtaposed above the cardstock layer 800. The barrier film layer 200 is juxtaposed above the actives/product layer 100. The heater layer 300 is juxtaposed above the barrier film layer 200. In this embodiment, the layers 100, 200, and 300, which are intended to remain as a unit, are provided in the shape of the mask that is placed on the skin. The hydrogel heat activator 96 is coextensive and similar in shape to the heater layer 300 so that when the two halves of the card 94 are brought into contact, the hydrogel heat activator 96 is superposed on the heater layer 300.

In one embodiment, a package (10, 20, 30, 40, 50, 60, 70, 80, 90) comprises a mask (12, 22, 32, 42, 52, 62, 72, 89, 92) and an inactive heater 300, wherein the mask includes at least one product layer 100 having infused thereon at least one active, and wherein the inactive heater is located in or in proximity to the mask to transfer heat to the mask upon activation of the heater.

In one embodiment, a package (10, 20, 30, 40, 50, 60, 70, 80, 90) comprises a film 200 enclosing the inactive heater, wherein the film has an extensibility of 20% at a force of less than 70,000 lbs or less than 10,000 lbs or less than 25,000 lbs, or a bending length over time value of 3 mm to 65 mm at 10 mins.

In one embodiment, a package (10, 20, 30, 40, 50, 60, 70, 80, 90) comprises an adhesive layer on or the same as the product layer 100, wherein adhesive layer has a peel strength from 0.4 to 25 N/inch.

In one embodiment, the product layer 100 comprises a hydrogel or silicone film for adhering to the skin.

FIGS. 1 and 2

In one embodiment, a package 10 comprises a plurality of masks 12 each including an inactive heater 300, wherein the inactive heaters include a zinc air battery that is enclosed within a barrier film 500 with holes, each of the barrier films with holes is prescored and adhered releaseably to a common cover film 600.

In one embodiment, a package 10 comprises a substrate 400 juxtaposed next to the film 500 with holes, the heater 300 juxtaposed next to the substrate 400, a barrier film 200 juxtaposed next to the heater 300, and the product layer 100 juxtaposed next to the barrier film 200, wherein the product layer and cover film are exterior layers.

FIGS. 3 and 4

In one embodiment, the mask includes the inactive heater 300 which includes a zinc air battery that is enclosed within a barrier film 500 with holes, and a second barrier peel off film 600 is adhered over the holes preventing air to reach the battery 300.

In one embodiment, a package 20 comprises a substrate 400 juxtaposed next to the film with holes 500, the heater 300 juxtaposed next to the substrate 400, a barrier film 200 juxtaposed next to the heater 300, and the product layer 100 juxtaposed next to the barrier film 200, wherein the product layer and peel off film are exterior layers.

FIGS. 5 and 6

In one embodiment, the mask includes the inactive heater 300 which includes a zinc air battery that is enclosed within a barrier film with holes 500, and the barrier films with holes is prescored and adhered releaseably to a cover film 600 preventing air to reach the battery.

In one embodiment, a package 30 comprises a substrate 400 juxtaposed next to the film 500 with holes, the heater 300 juxtaposed next to the substrate, a barrier film 200 juxtaposed next to the heater 300, and the product layer 100 juxtaposed next to the barrier film 200, wherein the product layer and cover film are exterior layers.

FIGS. 7 and 8

In one embodiment, the mask includes the inactive heater 300 which includes a zinc air battery that is enclosed within a barrier film 500 with holes, wherein the mask with inactive heater are enclosed in cover film envelope 600, wherein the barrier film with holes is juxtaposed to the cover film envelope preventing air to reach the battery.

In one embodiment, a package 40 comprises a substrate 400 juxtaposed next to the film with holes 500, the heater 300 juxtaposed next to the substrate 400, and the product layer 100 juxtaposed next to the heater 300, wherein the product layer 100 and film 500 with holes are juxtaposed next to the opposite insides of the envelope 600.

FIGS. 9 and 10

In one embodiment, the mask and the inactive heater 300 which includes a zinc air battery that is enclosed within a barrier film 500 with holes are provided in a pouch 54 preventing air to reach the battery, wherein the mask is juxtaposed between the barrier film with holes and the pouch.

In one embodiment, a package 50 comprises a substrate 400 juxtaposed next to the heater 300, and the film 500 with holes is juxtaposed to the substrate 400, and the product layer 100 and heater 300 are juxtaposed next to opposite insides of the pouch 54.

FIGS. 11 and 12

In one embodiment, the mask and the inactive heater 300 which includes a zinc air battery are provided in a pouch 64 having barrier film 500 without holes on one side and holes on a second side, wherein a peel off film 600 is adhered releaseably over the holes preventing air to reach the battery, wherein the mask is juxtaposed next to the barrier film without holes.

In one embodiment, a package 60 comprises the heater 300 juxtaposed next to the film 500 with holes, a substrate 400 juxtaposed next to the heater 300, and the product layer 100 juxtaposed next to the substrate 400, wherein the product layer and heater are juxtaposed next to opposite insides of the pouch 64.

FIGS. 13 and 14

In one embodiment, the mask and the inactive heater 300 which includes a zinc air battery 300 that is enclosed within a barrier film 500 with holes are provided in a tray 71 preventing air to reach the battery, wherein the mask is juxtaposed between the barrier film with holes and the tray 71.

In one embodiment, a package 70 comprises a substrate 400 juxtaposed next to the heater 300, and the film 500 with holes juxtaposed next to the substrate 400, and the product layer 100 juxtaposed next to the film with holes 500, wherein the product layer and the heater are juxtaposed next to opposite insides of the tray 71.

FIGS. 15 and 16

In one embodiment, a package 80 comprises a stack of masks 89 in a tray 81 and a heater assembly 84 covering the stack of masks, wherein the heater assembly includes at least one inactive heater 300 which includes a zinc air battery enclosed in a barrier film 500 with holes and a peel off film 600 is adhered over the holes preventing air to reach the battery.

In one embodiment, the heater assembly 84 further comprises a substrate 400 juxtaposed next to the film with holes 500, the heater 300 is juxtaposed next to the substrate 400, and a cardstock 800 is juxtaposed next to the heater 300, wherein the cardstock and peel off film are exterior layers of the heater assembly 84.

FIGS. 17 and 18

In one embodiment, a package 90 comprises a card 94 capable of being folded to juxtapose a first side on a second opposite side, wherein the first side includes a mask 92 and the inactive heater 300 on the exterior, and the second side includes a hydrogel heat activator 96.

In one embodiment, a package 90 comprises a barrier film 200 juxtaposed next to the heater 300, the product layer 100 juxtaposed next to the barrier film 200, and the product layer juxtaposed next to the cardstock 800 on the first side.

FIG. 21

Figure 21:
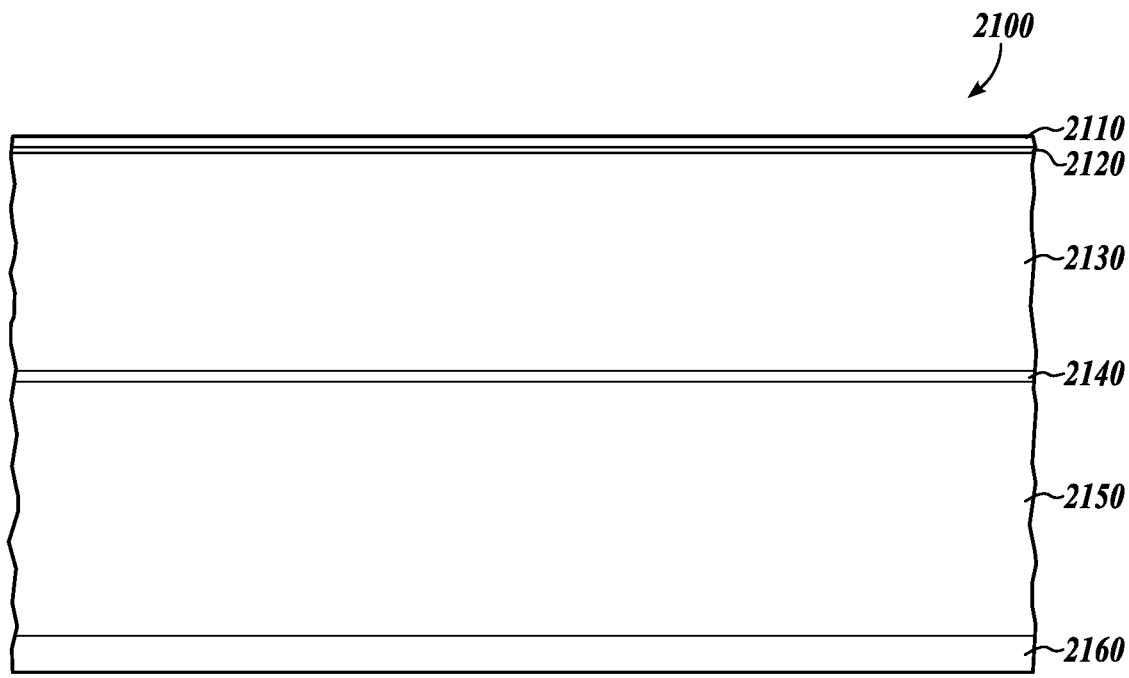
FIG. 21 is one embodiment of a package for a spot mask heater.
Figure 22:
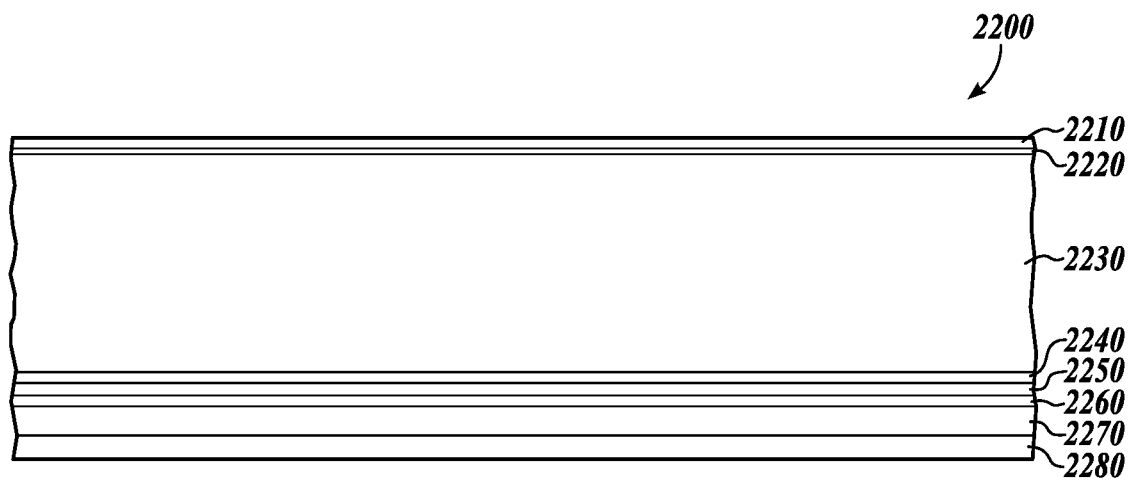
FIG. 22 is one embodiment of a package for a spot mask heater.

Referring to FIG. 21, in one embodiment, a package 2100 comprises a micro-cavitated PE (polyethylene) film 2120 juxtaposed next to the inactive heater 2130, a first metallized LDPE (low density polyethylene) film 2110 juxtaposed next to the micro-cavitated film 2120, and a second metallized LDPE film 2140 juxtaposed next to a side of inactive heater without the micro-cavitated film, wherein the first metallized LDPE film 2110 is on the exterior, and the product layer comprises a hydrogel layer 2150 juxtaposed next to the second metallized film 2140.

In one embodiment, a package 2100 comprises a PET (polyethylene terephthalate) release layer 2160 juxtaposed next to the hydrogel layer 2150, wherein the release layer is on the exterior.

FIG. 22

In one embodiment, a package 2200 comprises a micro-cavitated PE film 2220 juxtaposed next to the inactive heater 2230, a first metallized LDPE film 2210 juxtaposed next to the micro-cavitated PE film 2220, and a second metallized LDPE film 2240 juxtaposed next to a side of inactive heater 2230 without the micro-cavitated film, wherein the first metallized LDPE film 2210 is on the exterior, and the product layer comprises a silicone layer 2270 juxtaposed next to TPE (thermoplastic elastomer) carrier film 2260, wherein an acrylic adhesive 2250 layer is juxtaposed between the carrier film 2260 and the second LDPE metallized film 2240.

In one embodiment, a package 2200 comprises a release layer 2280 of Kraft paper juxtaposed next to the silicone layer 2270, wherein the release layer 2280 is on the exterior.

Metallized LDPE films are about 1.5 mils (mil=one-thousandth of inch). Micro-cavitated PE films are about 0.8 mils. Heaters are about 30 mils. Hydrogel layers are about 35 mils. PET release liners are about 5 mils. Acrylic adhesive layers are about 1.7 mils. TPE carrier films are about 1.5 mils. Silicone layers about 4 mils. Kraft paper release liners are about 3.3 mils. The above thicknesses have a range that extends above or below by 100%, or 50%, or 25%, or 10% of the stated thickness.

EXAMPLES

1. Example Demonstrating Peel Strength of Adhesive Product Layer

TABLE 1

Peel strength of various adhesive product layers

| # Sample | Peel test 1 (N/Inch) | Peel test 2 (N/Inch) |
| --- | --- | --- |
| 193B-65.7 | 22 | 25 |
| 193E-37 | 6 | 6.5 |
| 193G-35.9 | 4.8 | 4 |
| 193I-37.6 | 6.5 | 5.5 |
| 193F-67.3 | 10 | 8.4 |
| 193H-65.4 | 6.4 | 6 |
| 193J-67.2 | 8 | 8.8 |
| 193A-36.1 | 9 | 8 |
| 193C-35.5 | 8 | 8.7 |
| 193D-66.4 | 11.5 | 12.5 |
| 92892-Silicone | 16.2 | 16.5 |
| 93257-PU | 3 | 2.5 |
| 93276-nonwoven | 3.5 | 3 |
| AG625-Sensing Gel | 4 | 4 |
| AG735-Sensing Gel | 1 | 0.7 |
| AG548-Sensing Gel | 0.4 | 0.5 |

2. Example Demonstrating Film Conformability

Conformability experiments involved three different films of biaxially-oriented polypropylene (BOPP), low density polyethylene (PE), of polyacrylic acid (PA) at four different battery coat weight (0.2, 0.7, 1.2 and 1.5 g/si). The conformability of the battery package was measured by two prevalent methods used in health care which is used to estimate the conformability of wound care laminates. In one embodiment, conformability is measured according to EN 13726-4. In this method, the dressings are sectioned into 25 mm widths and marks made on the sample 100 mm apart (L1). The samples are then positioned within a tensometer then extended 20% and the maximum load recorded, so that the extensibility can be calculated (lb or N/cm). The sample is held at this extension for 1 min, then, removed from the tensometer. The 2 marks on the sample are then re-measured (L2) and the percentage of the permanent set is calculated.

Figure 19:
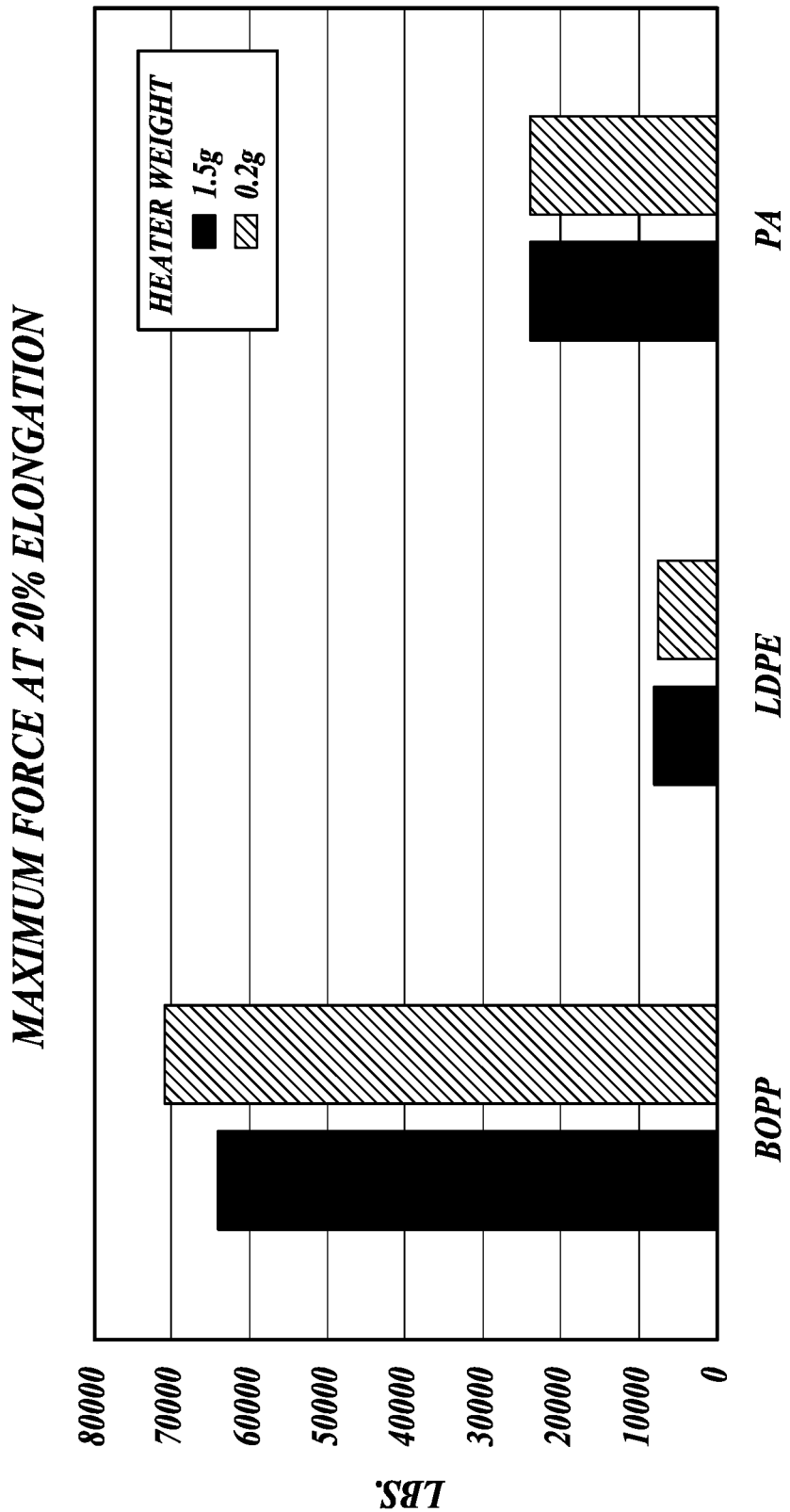
FIG. 19 is a bar graph comparing the bending force of various heater coating materials at two different weights.
Figure 20A:
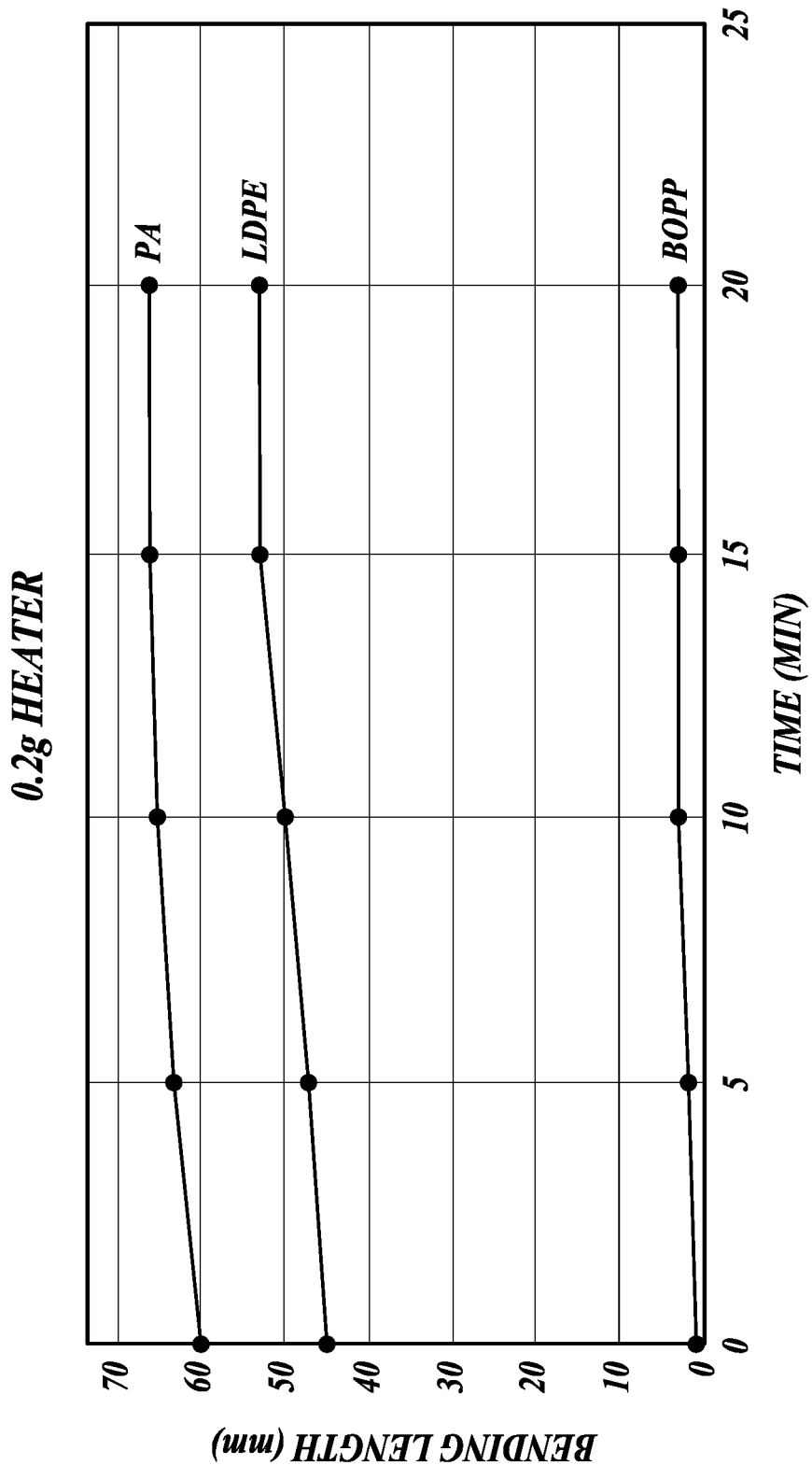
FIG. 20A is a graph of the bending length over time of various heater coating materials at a weight of 0.2 g/si (square inches)
Figure 20B:
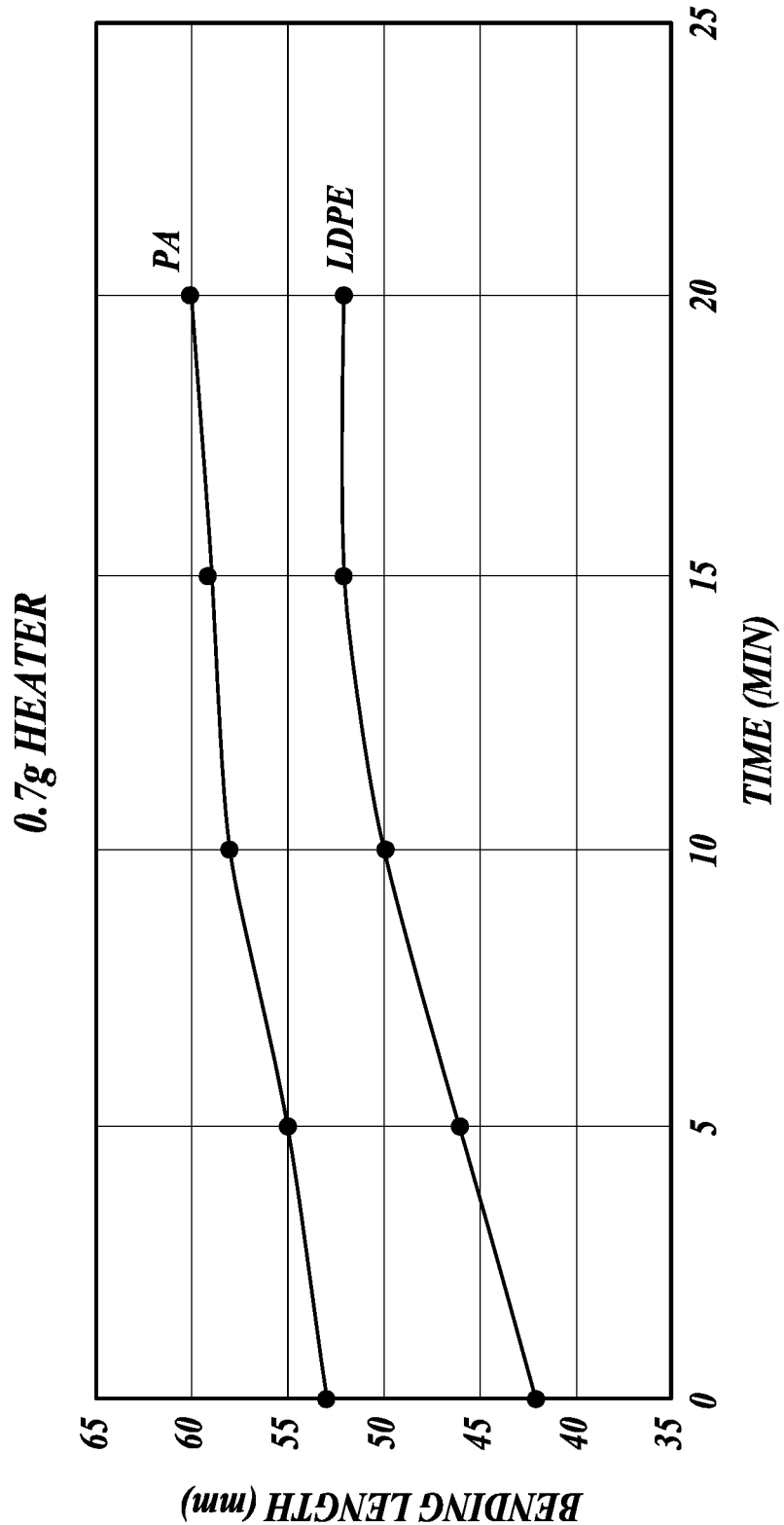
FIG. 20B is a graph of the bending length over time of various heater coating materials at a weight of 0.7 g/si.
Figure 20D:
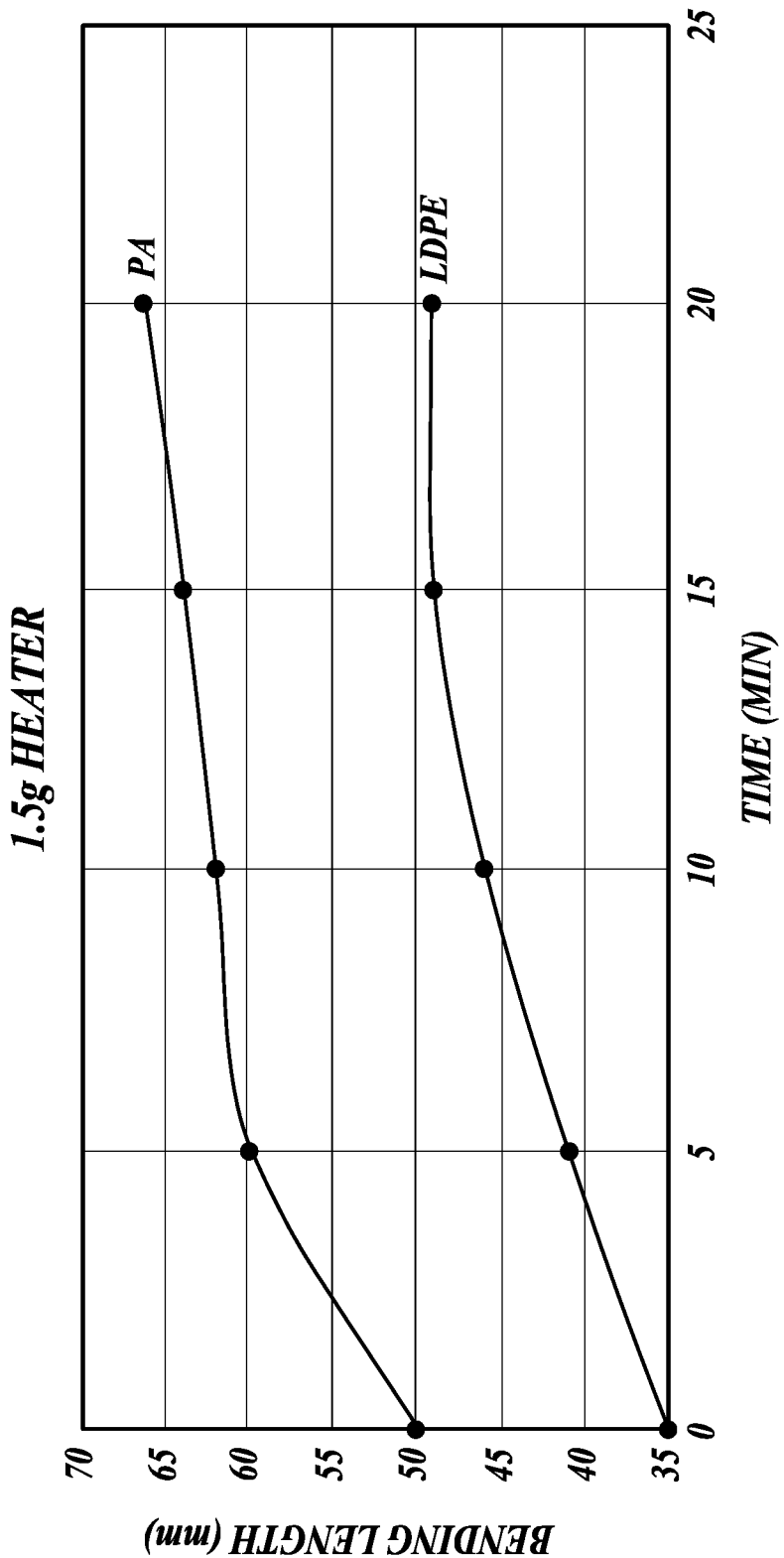
FIG. 20D is a graph of the bending length over time of various heater coating materials at a weight of 1.5 g/si.

The maximum force measured in 20% elongation of the battery pouch made with the highest (1.5 g/si) and the lowest (0.2 g/si) battery coat weights in three different packaging films demonstrate the flexibility is driven by the film. See FIG. 19.

The second test method correlates the bending length of a laminate to its conformability to curved surfaces of a patient body where a higher bending length corresponds to a more conformable laminate. See FIGS. 20A, 20B, 20C, and 20D A comparison of the bending of the samples at 10 minutes shows the packaging film has the larger effect on conformability of the laminate from the following Table.

TABLE 2

Bending Length (mm) of Battery Packs at 10 min

| Coating weight | 0.2 g/si | 0.7 g/si | 1.2 g/si | 1.5 g/si |
| --- | --- | --- | --- | --- |
| BOPP | 3 | 3 | 4 | 4 |
| PE | 50 | 50 | 49 | 46 |
| PA | 65 | 58 | 57 | 62 |

While illustrative embodiments have been illustrated and described, it will be appreciated that various changes can be made therein without departing from the spirit and scope of the invention.

The embodiments of the invention in which an exclusive property or privilege is claimed are defined as follows:

1. A package, comprising:
   a mask;
   an inactive heater, wherein the mask includes at least one product layer having infused thereon at least one active, and wherein the inactive heater is located in or in proximity to the mask to transfer heat to the mask upon activation of the heater, wherein the inactive heater is juxtaposed to a substrate on a first side and a barrier film on a second side, the substrate is juxtaposed to a film with holes, the film with holes is juxtaposed to a cover film, wherein the film with holes is coextensive with the cover film, and the film with holes is prescored in a shape of the mask to lift the mask from the cover film to activate the heater, wherein the substrate is a micro-cavitated film; and
   the product layer juxtaposed next to the barrier film, wherein the product layer and cover film are exterior layers.

2. The package of claim 1, comprising a film enclosing the inactive heater, wherein the film has a conformability measured by an extensibility of 20% at a force of less than 70,000 lbs or less than 10,000 lbs or less than 25,000 lbs, or a bending length over time value of 3 mm to 65 mm at 10 mins.

3. The package of claim 1, comprising an adhesive layer on or the same as the product layer, wherein adhesive layer has a peel strength from 0.4 to 25 N/inch.

4. The package of claim 1, wherein the product layer comprises a hydrogel or silicone film for adhering to the skin.

5. The package of claim 1, comprising a plurality of masks each including an inactive heater, wherein the inactive heaters include a zinc air battery that is enclosed within a barrier film with holes, each of the barrier films with holes is prescored and adhered releaseably to a common cover film.

* * * * *